US012778977B2

(12) United States Patent
Davidson et al.

(10) Patent No.: US 12,778,977 B2
(45) Date of Patent: Nov. 3, 2026

(54) COMBINED TRANSGENE AND INTRON-DERIVED MIRNA THERAPY FOR TREATMENT OF SCA1

(71) Applicant: THE CHILDREN'S HOSPITAL OF PHILADELPHIA, Philadelphia, PA (US)

(72) Inventors: Beverly L. Davidson, Philadelphia, PA (US); Ellie Carrell, Philadelphia, PA (US); Alejandro Mas Monteys, Philadelphia, PA (US); Megan S. Keiser, Philadelphia, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 1186 days.

(21) Appl. No.: 17/632,587

(22) PCT Filed: Aug. 14, 2020

(86) PCT No.: PCT/US2020/046499

§ 371 (c)(1),
(2) Date: Feb. 3, 2022

(87) PCT Pub. No.: WO2021/030745

PCT Pub. Date: Feb. 18, 2021

(65) Prior Publication Data

US 2022/0288101 A1 Sep. 15, 2022

Related U.S. Application Data

(60) Provisional application No. 62/887,209, filed on Aug. 15, 2019.

(51) Int. Cl.

*A61K 31/713* (2006.01)
*A61P 25/00* (2006.01)
*C12N 15/63* (2006.01)

(52) U.S. Cl.

CPC ............ *A61K 31/713* (2013.01); *A61P 25/00* (2018.01); *C12N 15/63* (2013.01); *C12N 2310/141* (2013.01); *C12N 2310/3519* (2013.01); *C12N 2330/51* (2013.01); *C12N 2750/14143* (2013.01)

(58) Field of Classification Search

CPC ....... A61K 31/713; A61K 45/06; A61P 25/00; C12N 15/63; C12N 2310/141; C12N 2310/3519; C12N 2330/51; C12N 2750/14143; C12N 15/113; C12N 2320/31; C07K 14/4702

See application file for complete search history.

(56) References Cited

U.S. PATENT DOCUMENTS 7,001,733 B1 * 2/2006 Ferrick ................ C12Q 1/6897 435/8
9,523,093 B2 * 12/2016 Davidson ................ A61P 25/14
2009/0130751 A1 * 5/2009 Davidson ............. C12N 15/113 536/23.1
2010/0063134 A1 3/2010 Kaemmerer et al.
2017/0298350 A1 * 10/2017 Eveleth .................. C12N 15/85
2017/0335318 A1 * 11/2017 Davidson ............... C12N 15/86
2017/0369877 A1 12/2017 Davidson et al.
2018/0169269 A1 6/2018 Davidson et al.
2019/0071671 A1 3/2019 Davidson et al.
2019/0117856 A1 * 4/2019 Schneiderman ........ A61L 31/06

FOREIGN PATENT DOCUMENTS

WO WO2015/143418 9/2015
WO WO 2016/196507 12/2016
WO WO-2016196507 A1 * 12/2016 ............. C07K 14/47
WO WO2017/151823 9/2017
WO WO-2019051255 A1 * 3/2019 ............. C12N 15/66
WO WO-2019113266 A1 * 6/2019 .............. A61P 25/08
WO WO 2020/033473 2/2020

OTHER PUBLICATIONS

Keiser, Megan S., et al. "RNAi or overexpression: alternative therapies for Spinocerebellar Ataxia Type 1." Neurobiology of disease 56 (2013): 6-13.. (Year: 2013).*

GenBank(hATXN1L), Accession NM_001137675 XM_928464, *Homo sapiens* ataxin 1 like (ATXN1L), mRNA, https://www.ncbi.nlm.nih.gov/nuccore/401709969?sat=46&satkey=134647227, retrieved Aug. 14, 2025, revision Dec. 6, 2017, printed as pp. 1/1 to 1/5. (Year: 2017).*

GenBank2, hATXN1L genomic sequence, *Homo sapiens* chromosome 16 clone RP11-498D10, complete sequence, Accession AC009127, (https://www.ncbi.nlm.nih.gov/nucleotide/AC009127.10?report=genbank&log$=nuclalign&blast_rank=2&RID=9VXUBNJ9013&from=155056&to=166408, retrieved Aug. 14, 2025, revision from Jan. 3, 2024,. (Year: 2018).*

Adlakha & Saini, "Brain microRNAs and insights into biological functions and therapeutic potential of brain enriched miRNA-128," Mol. Cancer, 13:33, 2014.

Banfi et al., "Identification and characterization of the gene causing type 1 spinocerebellar ataxia," *Nat. Genet.*, 7:513-520, 1994.

Boudreau et al., "Artificial microRNAs as siRNA shuttles: improved safety as compared to shRNAs in vitro and in vivo," *Mol. Ther.*, 17:169-175, 2009.

Bowman et al., "Duplication of Atxn11 suppresses SCA1 neuropathology by decreasing incorporation of polyglutamine-expanded ataxin-1 into native complexes," *Nat Genet.*, 39:373-379, 2007.

(Continued)

*Primary Examiner* — Ekaterina Poliakova-Georgantas
*Assistant Examiner* — John Charles Mckillop
(74) *Attorney, Agent, or Firm* — pH IP Law

(57) ABSTRACT

Provided herein are nucleic acids that comprise both an expression cassette for a therapeutic protein (e.g., Ataxin-1-like) and an expression cassette for a therapeutic inhibitory RNA (e.g., a miRNA that targets ataxin-1 mRNA). In some instances, the expression cassette for the therapeutic inhibitor RNA lies within an intron of the expression cassette for the therapeutic protein. Also provided are methods of using the nucleic acids to treat spinocerebellar.

17 Claims, 16 Drawing Sheets

Specification includes a Sequence Listing.

(56) References Cited

OTHER PUBLICATIONS

Burright et al., "SCA1 transgenic mice: a model for neurodegeneration caused by an expanded CAG trinucleotide repeat," *Cell*, 82:937-948, 1995.
Cong et al., "Multiplex genome engineering using CRISPR/Cas systems," *Science*, 339:819-823, 2013.
Cvetanovic et al., "The role of LANP and ataxin 1 in E4F-mediated transcriptional repression," *EMBO Rep.*, 8:671-677, 2007.
Extended Supplemental European Search Report for EP20851939.7 dated Aug. 28, 2023, 6 pages.
Guyenet et al., "A simple composite phenotype scoring system for evaluating mouse models of cerebellar ataxia," *J. Vis. Exp.*, 2010(39):1787, 2010.
Keiser et al., "Broad therapeutic benefit after RNAi expression vector delivery to deep cerebellar nuclei: implications for spinocerebellar ataxia type 1 therapy," *Mol. Ther.*, 22:588-595, 2014.
Keiser et al., "RNAi or overexpression: Alternative therapies for Spinocerebeller Ataxia Type 1," *Neurobiology of Disease*, 56:6-13, 2013.
Keiser et al., "RNAi prevents and reverses phenotypes induced by mutant human Ataxin-1," *Ann. Neruol.*, 80:754-765, 2016.
Lai et al., "14-3-3 Binding to ataxin-1(ATXN1) regulates its dephosphorylation at Ser-776 and transport to the nucleus," *J. Biol. Chem.*, 286:34606-34616, 2011.
Lam et al., "ATAXIN-1 interacts with the repressor Capicua in its native complex to cause SCA1 neuropathology," *Cell*, 127:1335-1347, 2006.
Lambrechts & Carmeliet, "VEGF at the neurovascular interface: therapeutic implications for motor neuron disease," *Biochim. Biophys. Acta*, 1762:1109-1121, 2006.
Lim et al., "Opposing effects of polyglutamine expansion on native protein complexes contribute to SCA1," *Nature*, 452:713-718, 2008.
Monteys et al., "CRISPR/Cas9 Editing of the Mutant Huntingtin Allele In Vitro and In Vivo," *Mol. Ther.*, 25:12-23, 2017.
Monteys et al., "Structure and activity of putative intronic miRNA promoters," *RNA*, 16:495-505, 2010.
Morrison et al., "The 14-3-3 proteins: integrators of diverse signaling cues that impact cell fate and cancer development," *Trends Cell Biol*, 19:16-23, 2009.
Orr et al., "Expansion of an unstable trinucleotide CAG repeat in spinocerebellar ataxia type 1," *Nat. Genet.*, 4:221-226, 1993.
Orr et al., "Polyglutamine neurodegeneration: expanded glutamines enhance native functions," *Curr. Opin. Genet. Dev.*, 2012. 22:251-255, 2012.
Oz et al., "Assessing recovery from neurodegeneration in spinocerebellar ataxia 1: Comparison of in vivo magnetic resonance spectroscopy with motor testing, gene expression and histology," *Neurobiol. Dis.*, 74C:158-166, 2014.
Oz et al., "In vivo monitoring of recovery from neurodegeneration in conditional transgenic SCA1 mice," *Exp Neurol*, 232:290-298, 2011.
Oz et al., "Noninvasive detection of presymptomatic and progressive neurodegeneration in a mouse model of spinocerebellar ataxia type 1," *J. Neurosci.*, 30:3831-3838, 2010.
PCT International Search Report and Written Opinion issued in International Application No. PCT/US2020/046499, dated Nov. 24, 2020.
PCT International Preliminary Report on Patentability for PCT/US2020/046499, dated Feb. 8, 2022.
Rodriguez-Lebron et al., "Altered Purkinje cell miRNA expression and SCA1 pathogenesis," Neurobiol. Dis., 54:456-463, 2013.
Serra et al., "Gene profiling links SCA1 pathophysiology to glutamate signaling in Purkinje cells of transgenic mice," *Hum. Mol. Genet.*, 13:2535-2543, 2004.
Serra et al., "RORalpha-mediated Purkinje cell development determines disease severity in adult SCA1 mice," *Cell*, 127:697-708, 2006.
Servadio et al., "Expression analysis of the ataxin-1 protein in tissues from normal and spinocerebellar ataxia type 1 individuals," Nat. Genet., 10:94-98, 1995.
Sternberg et al., "DNA interrogation by the CRISPR RNA-guided endonuclease Cas9," *Nature*, 507:62-67, 2014.
Tsuda et al., "The AXH domain of Ataxin-1 mediates neurodegeneration through its interaction with Gfi-1/Senseless proteins," *Cell*, 122:633-644, 2005.
Xia et al., "RNAi suppresses polyglutamine-induced neurodegeneration in a model of spinocerebellar ataxia," Nat. Med., 10:816-820, 2004.
Xia et al., "siRNA-mediated gene silencing in vitro and in vivo," *Nat. Biotechnol.*, 20:1006-1010, 2002.
Zoghbi & Orr, "Pathogenic mechanisms of a polyglutamine-mediated neurodegenerative disease, spinocerebellar ataxia type 1," *J Biol Chem*, 284:7425-7429, 2009.
Zu et al., "Recovery from polyglutamine-induced neurodegeneration in conditional SCA1 transgenic mice," *J. Neurosci.*, 24:8853-8861, 2004.
Carrell et al., Combined overexpression of ATXNIL and Mutant ATXN1 knockdown by AAV rescue motor phenotypes and gene signatures in SCA1 mice; *Molecular Therapy. Methods & Clinical Development*; 25, 333-343, 2022.
Curtis et al., "Knockdown and replacement therapy mediated by artificial mirtrons in spinocerebellar ataxia 7", *Nucleic Acids Research*, 45(13):7870-7885, 2017.
Pre-Appeal Examination Report for Japanese Application No. 2025-011355 dated Nov. 17, 2025, 6 pages.

* cited by examiner

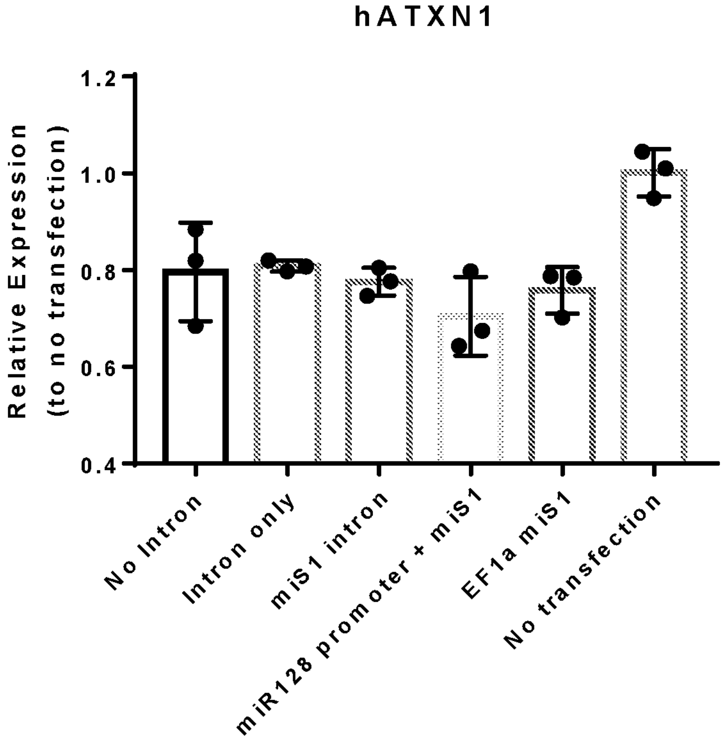
FIG. 2D
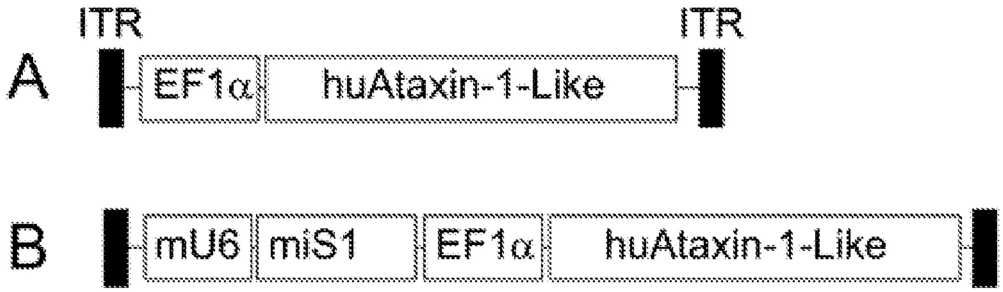
FIGS. 3A-B

```
SEQUENCE LISTING

<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 1

ucgaucuuca ggucguugcu u                                                 21


<210> SEQ ID NO 2
<211> LENGTH: 3888
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1373)..(3442)
<223> OTHER INFORMATION: hATXN1L coding sequence
<220> FEATURE:
<221> NAME/KEY: misc_feature
<222> LOCATION: (3447)..(3666)
<223> OTHER INFORMATION: bGH polyA
<220> FEATURE:
<221> NAME/KEY: misc_feature
<222> LOCATION: (3748)..(3888)
<223> OTHER INFORMATION: AAV2 ITR

<400> SEQUENCE: 2

cctgcaggca gctgcgcgct cgctcgctca ctgaggccgc ccgggcgtcg ggcgaccttt       60

ggtcgcccgg cctcagtgag cgagcgagcg cgcagagagg gagtggccaa ctccatcact      120

aggggttcct tgtagttaat gattaacccg ccatgctact tatctacgta gccatgctct      180

agtgaattcg tgaggctccg gtgcccgtca gtgggcagag cgcacatcgc ccacagtccc      240
```

```
cgagaagttg gggggagggg tcggcaattg aaccggtgcc tagagaaggt ggcgcggggt    300
aaactgggaa agtgatgtcg tgtactggct ccgccttttt cccgagggtg ggggagaacc    360
gtatataagt gcagtagtcg ccgtgaacgt tctttttcgc aacgggtttg ccgccagaac    420
acaggtaagt gccgtgtgtg gttcccgcgg gcctggcctc tttacgggtt atggcccttg    480
cgtgccttga attacttcca cctggctcca gtacgtgatt cttgatcccg agctggagcc    540
aggggcgggc cttgcgcttt aggagcccct tcgcctcgtg cttgagttga ggcctggcct    600
gggcgctggg gccgccgcgt gcgaatctgg tggcaccttc gcgcctgtct cgctgctttc    660
gataagtctc tagccattta aaatttttga tgacctgctg cgacgctttt tttctggcaa    720
gatagtcttg taaatgcggg ccaggatctg cacactggta tttcggtttt tgggcccgcg    780
gccggcgacg gggcccgtgc gtcccagcgc acatgttcgg cgaggcgggg cctgcgagcg    840
cggccaccga gaatcggacg ggggtagtct caagctggcc ggcctgctct ggtgcctggc    900
ctcgcgccgc cgtgtatcgc cccgccctgg gcggcaaggc tggcccggtc ggcaccagtt    960
gcgtgagcgg aaagatggcc gcttcccggc cctgctccag ggggctcaaa atggaggacg   1020
cggcgctcgg gagagcgggc gggtgagtca cccacacaaa ggaaaagggc ctttccgtcc   1080
tcagccgtcg cttcatgtga ctccacggag taccgggcgc cgtccaggca cctcgattag   1140
ttctggagct tttggagtac gtcgtcttta ggttgggggg aggggtttta tgcgatggag   1200
tttccccaca ctgagtgggt ggagactgaa gttaggccag cttggcactt gatgtaattc   1260
tcgttggaat ttgccctttt tgagtttgga tcttggttca ttctcaagcc tcagacagtg   1320
gttcaaagtt tttttcttcc atttcaggtg tcgtgaacac gtggtcgcca ccatgaaacc   1380
tgttcatgaa aggagtcagg aatgccttcc accaaagaaa cgagacctcc ccgtgaccag   1440
cgaggatatg ggagaaacta ccagctgctc cactaaccac acaccctcca gtgatgcttc   1500
tgaatggtcc cgaggggttg tggtggctgg gcagagccag gcaggagcca gagtcagcct   1560
ggggggtgat ggagctgagg ccatcaccgg tctgacagtg gaccagtatg gcatgctgta   1620
taaggtggct gtgccgcctg ccaccttttc accaactgga ctcccatctg tggtgaatat   1680
gagtcccttg cccccaacgt ttaatgtagc gtcttcacta attcaacatc caggcatcca   1740
ctatcctcca ctccactatg ctcagctccc atccacctcg ctgcagttca ttgggtctcc   1800
ttatagcctt ccctatgctg tgccacctaa tttcctaccg agtcccctcc tatctccttc   1860
tgccaacctt gccacctctc accttccaca ctttgtgcca tatgcctcac ttctggctga   1920
aggagccact cctcccccac aggctccctc cccggcccac tcatttaaca aagctccctc   1980
tgccacctcc ccatctgggc aattgccaca tcattcaagt actcagccgc tggaccttgc   2040
tccaggtcgg atgcccattt attatcagat gtccaggcta cctgctgggt atactttgca   2100
tgaaacccct ccagcaggtg ccagcccagt tcttacccct caggagagcc agtctgctct   2160
ggaagcagct gctgcaaatg gaggacagag accacgagag cgaaatttag taagacggga   2220
aagtgaagcc cttgactccc ccaacagcaa gggtgaaggc cagggactgg tgccagtggt   2280
agaatgtgtg gtggatggac agttgttttc aggttctcag actccacggg tagaggtagc   2340
agcaccagca caccgggga ccccggacac tgaccttgag gtccagcggg tggttggcgc   2400
tttagcttct caggactatc gtgtggtggc agctcagagg aaggaggaac ccagcccccct   2460
caacctatcc catcataccc ccgaccatca gggtgagggg cgagggtcag ccaggaaccc   2520
tgcagagctg gcagagaaaa gtcaggcccg tgggttctac cctcagtccc atcaggaacc   2580
```

agtaaaacat agacctttac ccaaagcaat ggttgtagcc aatggcaacc tggtgcccac 2640
tggaactgac tcaggcctgc tgcctgtggg ctcggagatc ctggtagcat caagtctgga 2700
cgtgcaggcc agagccacct tcccagacaa ggagccaacg ccgcccccca ttacctcctc 2760
tcacttgcct tcccatttca tgaaaggcgc catcatccag ctggctacgg gagagctgaa 2820
gcgggtggag gacctccaga cccaggattt tgtgcgcagt gccgaagtga gcggggggct 2880
gaagattgac tctagcacgg tcgtggacat tcaggagagc caatggcctg gatttgtcat 2940
gctgcatttt gtggttggtg agcagcagag caaagtgagc atcgaagtgc cccccgagca 3000
ccccttcttt gtatatggcc agggttggtc ctcttgcagc cctgggcgga cgacacaact 3060
cttctctctg ccctgccatc ggctacaggt gggagatgtc tgcatctcta tcagtttaca 3120
gagcttgaac agtaactcag tttctcaggc cagctgtgct cccccaagcc agctgggtcc 3180
cccccgagaa aggcctgaga ggacggtctt gggatccaga gagctatgtg acagtgaggg 3240
gaagagccag ccggcaggag agggctcccg tgtggtagag ccttcccagc ctgagtccgg 3300
tgctcaggcc tgctggccag ccccgagctt ccaaagatac agcatgcaag gggaggaggc 3360
acgggctgcg ctgctccgtc cctctttcat tccacaggag gtaaagctgt ccattgaagg 3420
gcgttccaat gcgggaaaat gagattctag ccctcgactg tgccttctag ttgccagcca 3480
tctgttgttt gcccctcccc cgtgccttcc ttgaccctgg aaggtgccac tcccactgtc 3540
ctttcctaat aaaatgagga aattgcatcg cattgtctga gtaggtgtca ttctattctg 3600
gggggtgggg tggggcagga cagcaagggg gaggattggg aagacaatag caggcatgct 3660
ggggagtcga ccctgcaagg tgagtgtaaa gaacactaga gcaaggctac gtagataagt 3720
agcatggcgg gttaatcatt aactacaagg aacccctagt gatggagttg gccactccct 3780
ctctgcgcgc tcgctcgctc actgaggccg ggcgaccaaa ggtcgcccga cgcccgggct 3840
ttgcccgggc ggcctcagtg agcgagcgag cgcgcagctg cctgcagg 3888

<210> SEQ ID NO 3
<211> LENGTH: 4741
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1364)..(1425)
<223> OTHER INFORMATION: hATXN1L non-coding exon 2
<220> FEATURE:
<221> NAME/KEY: misc_feature
<222> LOCATION: (1426)..(2108)
<223> OTHER INFORMATION: modified hATXN1L intron 2
<220> FEATURE:
<221> NAME/KEY: misc_feature
<222> LOCATION: (2109)..(2225)
<223> OTHER INFORMATION: hATXN1L non-coding exon 3
<220> FEATURE:
<221> NAME/KEY: misc_feature
<222> LOCATION: (2226)..(4295)
<223> OTHER INFORMATION: hATXN1L coding sequence
<220> FEATURE:
<221> NAME/KEY: misc_feature
<222> LOCATION: (4300)..(4519)
<223> OTHER INFORMATION: bGH polyA
<220> FEATURE:
<221> NAME/KEY: misc_feature
<222> LOCATION: (4601)..(4741)
<223> OTHER INFORMATION: AAV2 ITR

<400> SEQUENCE: 3

```
cctgcaggca gctgcgcgct cgctcgctca ctgaggccgc ccgggcgtcg ggcgaccttt      60

ggtcgcccgg cctcagtgag cgagcgagcg cgcagagagg gagtggccaa ctccatcact     120

aggggttcct tgtagttaat gattaacccg ccatgctact tatctacgta gccatgctct     180

agtgaattcg tgaggctccg gtgcccgtca gtgggcagag cgcacatcgc ccacagtccc     240

cgagaagttg gggggagggg tcggcaattg aaccggtgcc tagagaaggt ggcgcggggt     300

aaactgggaa agtgatgtcg tgtactggct ccgccttttt cccgagggtg ggggagaacc     360

gtatataagt gcagtagtcg ccgtgaacgt tctttttcgc aacgggtttg ccgccagaac     420

acaggtaagt gccgtgtgtg gttcccgcgg gcctggcctc tttacgggtt atggcccttg     480

cgtgccttga attacttcca cctggctcca gtacgtgatt cttgatcccg agctggagcc     540

aggggcgggc cttgcgcttt aggagcccct tcgcctcgtg cttgagttga ggcctggcct     600

gggcgctggg gccgccgcgt gcgaatctgg tggcaccttc gcgcctgtct cgctgctttc     660

gataagtctc tagccattta aaatttttga tgacctgctg cgacgctttt tttctggcaa     720

gatagtcttg taaatgcggg ccaggatctg cacactggta tttcggtttt tgggcccgcg     780

gccggcgacg gggcccgtgc gtcccagcgc acatgttcgg cgaggcgggg cctgcgagcg     840

cggccaccga gaatcggacg ggggtagtct caagctggcc ggcctgctct ggtgcctggc     900

ctcgcgccgc cgtgtatcgc cccgccctgg gcggcaaggc tggcccggtc ggcaccagtt     960

gcgtgagcgg aaagatggcc gcttcccggc cctgctccag ggggctcaaa atggaggacg    1020

cggcgctcgg gagagcgggc gggtgagtca cccacacaaa ggaaaagggc ctttccgtcc    1080

tcagccgtcg cttcatgtga ctccacggag taccgggcgc cgtccaggca cctcgattag    1140

ttctggagct tttggagtac gtcgtcttta ggttgggggg aggggtttta tgcgatggag    1200

tttccccaca ctgagtgggt ggagactgaa gttaggccag cttggcactt gatgtaattc    1260

tcgttggaat ttgccctttt tgagtttgga tcttggttca ttctcaagcc tcagacagtg    1320

gttcaaagtt tttttcttcc atttcaggtg tcgtgaacac gtggctcccg agccagccgg    1380

gaggacactt actacagctg ctcagaagca ccactggaaa ctcaggtaat accggcactt    1440

tgaattcctt gtttcaggaa aatatctggg atgtcacagt ggaaaaacag aacagaatgt    1500

aatatagaaa gctcttttca gatccaaaga actggaacct ggttggaaga aataggcagc    1560

aaagttcatg tgcactgaag tgttcagacc aaaaagttgc tttataacaa tggacaaaag    1620

catttgtgaa aggtgacaat aagagaaaag ggaaagagaa ctttcttatg aatcatacag    1680

atacggggaa aaaaacaggc atgtttagag gaatggaacc agaatttcat ggagtggtgc    1740

ctggagcaga cttcgaaatt tcagctagct tcaacgcgtg gcagaaaaga gacaaggtgc    1800

ttatgagaca catgactaac cgtgaagctg ttggtctccc tgggcttgtg gagcccacag    1860

gttatttgtg cattggtgaa tgcgtgtccc tgtagctctt tgtgccttgt gatttccccg    1920

actgtttctc tcatgtccca ggctggatga gttgggggta gcctccttgt ctgccccttt    1980

ctctttcctc cttattttct aacagtcccc tttgttacat cttcctccat ggcacagttc    2040

tttctatttc ctttgtcttg gctcatccct aggttacttt tctttgcctc tgatttgttc    2100

cctaatagat gtgggcgccc cagccagaag cagagagggg tacagggaag ctacagagaa    2160
```

```
gccccttctg atgccccagg gagcaagtcg actccttcca ggctccagga acaccacaaa   2220
gcaatatgaa acctgttcat gaaaggagtc aggaatgcct tccaccaaag aaacgagacc   2280
tccccgtgac cagcgaggat atggggagaa ctaccagctg ctccactaac cacacaccct   2340
ccagtgatgc ttctgaatgg tcccgagggg ttgtggtggc tggcagagc caggcaggag    2400
ccagagtcag cctgggggt gatggagctg aggccatcac cggtctgaca gtggaccagt    2460
atggcatgct gtataaggtg gctgtgccgc ctgccacctt ttcaccaact ggactcccat   2520
ctgtggtgaa tatgagtccc ttgcccccaa cgtttaatgt agcgtcttca ctaattcaac   2580
atccaggcat ccactatcct ccactccact atgctcagct cccatccacc tcgctgcagt   2640
tcattgggtc tccttatagc cttccctatg ctgtgccacc taatttccta ccgagtcccc   2700
tcctatctcc ttctgccaac cttgccacct ctcaccttcc acactttgtg ccatatgcct   2760
cacttctggc tgaaggagcc actcctcccc cacaggctcc ctccccggcc cactcattta   2820
acaaagctcc ctctgccacc tccccatctg ggcaattgcc acatcattca agtactcagc   2880
cgctggacct tgctccaggt cggatgccca tttattatca gatgtccagg ctacctgctg   2940
ggtatacttt gcatgaaacc cctccagcag gtgccagccc agttcttacc cctcaggaga   3000
gccagtctgc tctggaagca gctgctgcaa atggaggaca gagaccacga gagcgaaatt   3060
tagtaagacg ggaaagtgaa gcccttgact cccccaacag caagggtgaa ggccagggac   3120
tggtgccagt ggtagaatgt gtggtggatg gacagttgtt ttcaggttct cagactccac   3180
gggtagaggt agcagcacca gcacaccggg ggaccccgga cactgacctt gaggtccagc   3240
gggtggttgg cgctttagct tctcaggact atcgtgtggt ggcagctcag aggaaggagg   3300
aacccagccc cctcaaccta tcccatcata cccccgacca tcagggtgag ggcgagggt    3360
cagccaggaa ccctgcagag ctggcagaga aaagtcaggc ccgtgggttc taccctcagt   3420
cccatcagga accagtaaaa catagacctt tacccaaagc aatggttgta gccaatggca   3480
acctggtgcc cactggaact gactcaggcc tgctgcctgt gggctcggag atcctggtag   3540
catcaagtct ggacgtgcag gccagagcca ccttcccaga caaggagcca acgccgcccc   3600
ccattacctc ctctcacttg ccttcccatt tcatgaaagg cgccatcatc cagctggcta   3660
cgggagagct gaagcgggtg gaggacctcc agacccagga ttttgtgcgc agtgccgaag   3720
tgagcggggg gctgaagatt gactctagca cggtcgtgga cattcaggag agccaatggc   3780
ctggatttgt catgctgcat tttgtggttg gtgagcagca gagcaaagtg agcatcgaag   3840
tgccccccga gcaccccttc tttgtatatg gccagggttg gtcctcttgc agccctgggc   3900
ggacgacaca actcttctct ctgccctgcc atcggctaca ggtgggagat gtctgcatct   3960
ctatcagttt acagagcttg aacagtaact cagtttctca ggccagctgt gctcccccaa   4020
gccagctggg tccccccga gaaaggcctg agaggacggt cttgggatcc agagagctat    4080
gtgacagtga ggggaagagc cagccggcag gagagggctc ccgtgtggta gagccttccc   4140
agcctgagtc cggtgctcag gcctgctggc cagccccgag cttccaaaga tacagcatgc   4200
aaggggagga ggcacgggct gcgctgctcc gtccctcttt cattccacag gaggtaaagc   4260
tgtccattga agggcgttcc aatgcgggaa aatgagattc tagccctcga ctgtgccttc   4320
tagttgccag ccatctgttg tttgcccctc ccccgtgcct tccttgaccc tggaaggtgc   4380
cactcccact gtcctttcct aataaaatga ggaaattgca tcgcattgtc tgagtaggtg   4440
tcattctatt ctggggggtg gggtggggca ggacagcaag ggggaggatt gggaagacaa   4500
tagcaggcat gctggggagt cgaccctgca aggtgagtgt aaagaacact agagcaaggc   4560
```

```
tacgtagata agtagcatgg cgggttaatc attaactaca aggaacccct agtgatggag   4620

ttggccactc cctctctgcg cgctcgctcg ctcactgagg ccgggcgacc aaaggtcgcc   4680

cgacgcccgg gctttgcccg ggcggcctca gtgagcgagc gagcgcgcag ctgcctgcag   4740

g                                                                   4741


<210> SEQ ID NO 4
<211> LENGTH: 4831
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1364)..(1425)
<223> OTHER INFORMATION: hATXN1L non-coding exon 2
<220> FEATURE:
<221> NAME/KEY: misc_feature
<222> LOCATION: (1426)..(2198)
<223> OTHER INFORMATION: modified hATXN1L intron 2
<220> FEATURE:
<221> NAME/KEY: misc_feature
<222> LOCATION: (1770)..(1863)
<223> OTHER INFORMATION: miR128
<220> FEATURE:
<221> NAME/KEY: misc_feature
<222> LOCATION: (2199)..(2315)
<223> OTHER INFORMATION: hATXN1L non-coding exon 3
<220> FEATURE:
<221> NAME/KEY: misc_feature
<222> LOCATION: (2316)..(4385)
<223> OTHER INFORMATION: hATXN1L coding sequence
<220> FEATURE:
<221> NAME/KEY: misc_feature
<222> LOCATION: (4390)..(4609)
<223> OTHER INFORMATION: bGH polyA
<220> FEATURE:
<221> NAME/KEY: misc_feature
<222> LOCATION: (4691)..(4831)
<223> OTHER INFORMATION: AAV2 ITR

<400> SEQUENCE: 4

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

agtgaattcg tgaggctccg gtgcccgtca gtgggcagag cgcacatcgc ccacagtccc    240

cgagaagttg gggggagggg tcggcaattg aaccggtgcc tagagaaggt ggcgcggggt    300

aaactgggaa agtgatgtcg tgtactggct ccgccttttt cccgagggtg ggggagaacc    360

gtatataagt gcagtagtcg ccgtgaacgt tctttttcgc aacgggtttg ccgccagaac    420

acaggtaagt gccgtgtgtg gttcccgcgg gcctggcctc tttacgggtt atggcccttg    480

cgtgccttga attacttcca cctggctcca gtacgtgatt cttgatcccg agctggagcc    540

aggggcgggc cttgcgcttt aggagcccct tcgcctcgtg cttgagttga ggcctggcct    600

gggcgctggg gccgccgcgt gcgaatctgg tggcaccttc gcgcctgtct cgctgctttc    660

gataagtctc tagccattta aaatttttga tgacctgctg cgacgctttt tttctggcaa    720
```

```
gatagtcttg taaatgcggg ccaggatctg cacactggta tttcggtttt tgggcccgcg    780
gccggcgacg gggcccgtgc gtcccagcgc acatgttcgg cgaggcgggg cctgcgagcg    840
cggccaccga gaatcggacg gggtagtctc caagctggcc ggcctgctct ggtgcctggc    900
ctcgcgccgc cgtgtatcgc cccgccctgg gcggcaaggc tggcccggtc ggcaccagtt    960
gcgtgagcgg aaagatggcc gcttcccggc cctgctccag gggctcaaa atggaggacg    1020
cggcgctcgg gagagcgggc gggtgagtca cccacacaaa ggaaaagggc ctttccgtcc   1080
tcagccgtcg cttcatgtga ctccacggag taccgggcgc cgtccaggca cctcgattag   1140
ttctggagct tttggagtac gtcgtcttta ggttgggggg aggggtttta tgcgatggag   1200
tttccccaca ctgagtgggt ggagactgaa gttaggccag cttggcactt gatgtaattc   1260
tcgttggaat ttgccctttt tgagtttgga tcttggttca ttctcaagcc tcagacagtg   1320
gttcaaagtt tttttcttcc atttcaggtg tcgtgaacac gtggctcccg agccagccgg   1380
gaggacactt actacagctg ctcagaagca ccactggaaa ctcaggtaat accggcactt   1440
tgaattcctt gtttcaggaa aatatctggg atgtcacagt ggaaaaacag aacagaatgt   1500
aatatagaaa gctcttttca gatccaaaga actggaacct ggttggaaga aataggcagc   1560
aaagttcatg tgcactgaag tgttcagacc aaaaagttgc tttataacaa tggacaaaag   1620
catttgtgaa aggtgacaat aagagaaaag ggaaagagaa ctttcttatg aatcatacag   1680
atacggggaa aaaaacaggc atgtttagag gaatggaacc agaatttcat ggagtggtgc   1740
ctggagcaga cttcgaaatt tcagctagct gtgcagtggg aagggggggcc gatacactgt  1800
acgagagtga gtagcaggtc tcacagtgaa ccggtctctt tccctactgt gtcacacttt   1860
tttacgcgtg gcagaaaaga gacaaggtgc ttatgagaca catgactaac cgtgaagctg   1920
ttggtctccc tgggcttgtg gagcccacag gttatttgtg cattggtgaa tgcgtgtccc   1980
tgtagctctt tgtgccttgt gatttccccg actgtttctc tcatgtccca ggctggatga   2040
gttgggggta gcctccttgt ctgccccttt ctctttcctc cttattttct aacagtcccc   2100
tttgttacat cttcctccat ggcacagttc tttctatttc ctttgtcttg gctcatccct   2160
aggttacttt tctttgcctc tgatttgttc cctaatagat gtgggcgccc cagccagaag   2220
cagagagggg tacagggaag ctacagagaa gccccttctg atgccccagg gagcaagtcg   2280
actccttcca ggctccagga acaccacaaa gcaatatgaa acctgttcat gaaaggagtc   2340
aggaatgcct tccaccaaag aaacgagacc tccccgtgac cagcgaggat atggggagaa   2400
ctaccagctg ctccactaac cacacaccct ccagtgatgc ttctgaatgg tcccgagggg   2460
ttgtggtggc tgggcagagc caggcaggag ccagagtcag cctgggggt gatggagctg    2520
aggccatcac cggtctgaca gtggaccagt atggcatgct gtataaggtg gctgtgccgc   2580
ctgccacctt ttcaccaact ggactcccat ctgtggtgaa tatgagtccc ttgcccccaa   2640
cgtttaatgt agcgtcttca ctaattcaac atccaggcat ccactatcct ccactccact   2700
atgctcagct cccatccacc tcgctgcagt tcattgggtc tccttatagc cttccctatg   2760
ctgtgccacc taatttccta ccgagtcccc tcctatctcc ttctgccaac cttgccacct   2820
ctcaccttcc acactttgtg ccatatgcct cacttctggc tgaaggagcc actcctcccc   2880
cacaggctcc ctccccggcc cactcattta acaaagctcc ctctgccacc tccccatctg   2940
ggcaattgcc acatcattca agtactcagc cgctggacct tgctccaggt cggatgccca   3000
tttattatca gatgtccagg ctacctgctg ggtatacttt gcatgaaacc cctccagcag   3060
gtgccagccc agttcttacc cctcaggaga gccagtctgc tctggaagca gctgctgcaa   3120
```

```
atggaggaca gagaccacga gagcgaaatt tagtaagacg ggaaagtgaa gcccttgact   3180

cccccaacag caagggtgaa ggccagggac tggtgccagt ggtagaatgt gtggtggatg   3240

gacagttgtt ttcaggttct cagactccac gggtagaggt agcagcacca gcacaccggg   3300

ggaccccgga cactgacctt gaggtccagc gggtggttgg cgctttagct tctcaggact   3360

atcgtgtggt ggcagctcag aggaaggagg aacccagccc cctcaaccta tcccatcata   3420

cccccgacca tcagggtgag gggcgagggt cagccaggaa ccctgcagag ctggcagaga   3480

aaagtcaggc ccgtgggttc taccctcagt cccatcagga accagtaaaa catagacctt   3540

tacccaaagc aatggttgta gccaatggca acctggtgcc cactggaact gactcaggcc   3600

tgctgcctgt gggctcggag atcctggtag catcaagtct ggacgtgcag gccagagcca   3660

ccttcccaga caaggagcca acgccgcccc ccattacctc ctctcacttg ccttcccatt   3720

tcatgaaagg cgccatcatc cagctggcta cgggagagct gaagcgggtg gaggacctcc   3780

agacccagga ttttgtgcgc agtgccgaag tgagcggggg gctgaagatt gactctagca   3840

cggtcgtgga cattcaggag agccaatggc ctggatttgt catgctgcat tttgtggttg   3900

gtgagcagca gagcaaagtg agcatcgaag tgccccccga gcaccccttc tttgtatatg   3960

gccagggttg gtcctcttgc agccctgggc ggacgacaca actcttctct ctgccctgcc   4020

atcggctaca ggtgggagat gtctgcatct ctatcagttt acagagcttg aacagtaact   4080

cagtttctca ggccagctgt gctcccccaa gccagctggg tcccccccga gaaaggcctg   4140

agaggacggt cttgggatcc agagagctat gtgacagtga ggggaagagc cagccggcag   4200

gagagggctc ccgtgtggta gagccttccc agcctgagtc cggtgctcag gcctgctggc   4260

cagccccgag cttccaaaga tacagcatgc aaggggagga ggcacgggct gcgctgctcc   4320

gtccctcttt cattccacag gaggtaaagc tgtccattga agggcgttcc aatgcgggaa   4380

aatgagattc tagccctcga ctgtgccttc tagttgccag ccatctgttg tttgcccctc   4440

ccccgtgcct tccttgaccc tggaaggtgc cactcccact gtcctttcct aataaaatga   4500

ggaaattgca tcgcattgtc tgagtaggtg tcattctatt ctggggggtg gggtggggca   4560

ggacagcaag ggggaggatt gggaagacaa tagcaggcat gctggggagt cgaccctgca   4620

aggtgagtgt aaagaacact agagcaaggc tacgtagata agtagcatgg cgggttaatc   4680

attaactaca aggaacccct agtgatggag ttggccactc cctctctgcg cgctcgctcg   4740

ctcactgagg ccgggcgacc aaaggtcgcc cgacgcccgg gctttgcccg ggcggcctca   4800

gtgagcgagc gagcgcgcag ctgcctgcag g                                  4831
```

<210> SEQ ID NO 5
<211> LENGTH: 4991
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1364)..(1425)
<223> OTHER INFORMATION: hATXN1L non-coding exon 2
<220> FEATURE:

<221> NAME/KEY: misc_feature
<222> LOCATION: (1426)..(2358)
<223> OTHER INFORMATION: modified hATXN1L intron 2
<220> FEATURE:
<221> NAME/KEY: misc_feature
<222> LOCATION: (1754)..(1930)
<223> OTHER INFORMATION: miR128 promoter
<220> FEATURE:
<221> NAME/KEY: misc_feature
<222> LOCATION: (1931)..(2023)
<223> OTHER INFORMATION: miR128
<220> FEATURE:
<221> NAME/KEY: misc_feature
<222> LOCATION: (2030)..(2358)
<223> OTHER INFORMATION: hATXN1L 3' intron 2
<220> FEATURE:
<221> NAME/KEY: misc_feature
<222> LOCATION: (2359)..(2475)
<223> OTHER INFORMATION: hATXN1L non-coding exon 3
<220> FEATURE:
<221> NAME/KEY: misc_feature
<222> LOCATION: (3476)..(4545)
<223> OTHER INFORMATION: hATXN1L coding sequence
<220> FEATURE:
<221> NAME/KEY: misc_feature
<222> LOCATION: (4550)..(4769)
<223> OTHER INFORMATION: bGH polyA
<220> FEATURE:
<221> NAME/KEY: misc_feature
<222> LOCATION: (4851)..(4991)
<223> OTHER INFORMATION: AAV2 ITR

<400> SEQUENCE: 5
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
agtgaattcg tgaggctccg gtgcccgtca gtgggcagag cgcacatcgc ccacagtccc 240
cgagaagttg gggggagggg tcggcaattg aaccggtgcc tagagaaggt ggcgcggggt 300
aaactgggaa agtgatgtcg tgtactggct ccgccttttt cccgagggtg ggggagaacc 360
gtatataagt gcagtagtcg ccgtgaacgt tctttttcgc aacgggtttg ccgccagaac 420
acaggtaagt gccgtgtgtg gttcccgcgg gcctggcctc tttacgggtt atggcccttg 480
cgtgccttga attacttcca cctggctcca gtacgtgatt cttgatcccg agctggagcc 540
aggggcgggc cttgcgcttt aggagcccct tcgcctcgtg cttgagttga ggcctggcct 600
gggcgctggg gccgccgcgt gcgaatctgg tggcaccttc gcgcctgtct cgctgctttc 660
gataagtctc tagccattta aaatttttga tgacctgctg cgacgctttt tttctggcaa 720
gatagtcttg taaatgcggg ccaggatctg cacactggta tttcggtttt tgggcccgcg 780
gccggcgacg gggcccgtgc gtcccagcgc acatgttcgg cgaggcgggg cctgcgagcg 840
cggccaccga gaatcggacg ggggtagtct caagctggcc ggcctgctct ggtgcctggc 900
ctcgcgccgc cgtgtatcgc cccgccctgg gcggcaaggc tggcccggtc ggcaccagtt 960
gcgtgagcgg aaagatggcc gcttcccggc cctgctccag ggggctcaaa atggaggacg 1020
cggcgctcgg gagagcgggc gggtgagtca cccacacaaa ggaaaagggc ctttccgtcc 1080
tcagccgtcg cttcatgtga ctccacggag taccgggcgc cgtccaggca cctcgattag 1140
ttctggagct tttggagtac gtcgtcttta ggttgggggg aggggtttta tgcgatggag 1200
tttccccaca ctgagtgggt ggagactgaa gttaggccag cttggcactt gatgtaattc 1260
tcgttggaat ttgccctttt tgagtttgga tcttggttca ttctcaagcc tcagacagtg 1320
gttcaaagtt tttttcttcc atttcaggtg tcgtgaacac gtggctcccg agccagccgg 1380
gaggacactt actacagctg ctcagaagca ccactggaaa ctcaggtaat accggcactt 1440
tgaattcctt gtttcaggaa aatatctggg atgtcacagt ggaaaaacag aacagaatgt 1500
aatatagaaa gctcttttca gatccaaaga actggaacct ggttggaaga aataggcagc 1560
aaagttcatg tgcactgaag tgttcagacc aaaaagttgc tttataacaa tggacaaaag 1620
catttgtgaa aggtgacaat aagagaaaag ggaaagagaa ctttcttatg aatcatacag 1680
atacggggaa aaaaacaggc atgtttagag gaatggaacc agaatttcat ggagtggtgc 1740
ctggagcaga cttcgaagct tcctctgttc ttaaggctag ggaaccaaat taggttgttt 1800
caatatcgtg ctaaaagata ctgcctttag aagaaggcta ttgacaatcc agcgtgtctc 1860
ggtggaactc tgactccatg gttcactttc atgatggcca catgcctcct gcccagagcc 1920
cggcagccac tgtgcagtgg gaaggggggc cgatacactg tacgagagtg agtagcaggt 1980
ctcacagtga accggtctct ttccctactg tgtcacactt tttacgcgtg gcagaaaaga 2040
gacaaggtgc ttatgagaca catgactaac cgtgaagctg ttggtctccc tgggcttgtg 2100
gagcccacag gttatttgtg cattggtgaa tgcgtgtccc tgtagctctt tgtgccttgt 2160
gatttccccg actgtttctc tcatgtccca ggctggatga gttgggggta gcctccttgt 2220
ctgccccttt ctctttcctc cttattttct aacagtcccc tttgttacat cttcctccat 2280
ggcacagttc tttctatttc ctttgtcttg gctcatccct aggttacttt tctttgcctc 2340
tgatttgttc cctaatagat gtgggcgccc cagccagaag cagagagggg tacagggaag 2400
ctacagagaa gccccttctg atgccccagg gagcaagtcg actccttcca ggctccagga 2460
acaccacaaa gcaatatgaa acctgttcat gaaaggagtc aggaatgcct tccaccaaag 2520
aaacgagacc tccccgtgac cagcgaggat atggggagaa ctaccagctg ctccactaac 2580
cacacaccct ccagtgatgc ttctgaatgg tcccgagggg ttgtggtggc tgggcagagc 2640
caggcaggag ccagagtcag cctgggggt gatggagctg aggccatcac cggtctgaca 2700
gtggaccagt atggcatgct gtataaggtg gctgtgccgc ctgccacctt ttcaccaact 2760
ggactcccat ctgtggtgaa tatgagtccc ttgcccccaa cgtttaatgt agcgtcttca 2820
ctaattcaac atccaggcat ccactatcct ccactccact atgctcagct cccatccacc 2880
tcgctgcagt tcattgggtc tccttatagc cttccctatg ctgtgccacc taatttccta 2940
ccgagtcccc tcctatctcc ttctgccaac cttgccacct ctcaccttcc acactttgtg 3000
ccatatgcct cacttctggc tgaaggagcc actcctcccc cacaggctcc ctccccggcc 3060
cactcattta acaaagctcc ctctgccacc tccccatctg ggcaattgcc acatcattca 3120
agtactcagc cgctggacct tgctccaggt cggatgccca tttattatca gatgtccagg 3180
ctacctgctg ggtatacttt gcatgaaacc cctccagcag gtgccagccc agttcttacc 3240
cctcaggaga gccagtctgc tctggaagca gctgctgcaa atggaggaca gagaccacga 3300
gagcgaaatt tagtaagacg ggaaagtgaa gcccttgact cccccaacag caagggtgaa 3360
ggccagggac tggtgccagt ggtagaatgt gtggtggatg gacagttgtt ttcaggttct 3420
cagactccac gggtagaggt agcagcacca gcacaccggg ggaccccgga cactgacctt 3480
gaggtccagc gggtggttgg cgctttagct tctcaggact atcgtgtggt ggcagctcag 3540
aggaaggagg aacccagccc cctcaaccta tcccatcata cccccgacca tcagggtgag 3600
gggcgagggt cagccaggaa ccctgcagag ctggcagaga aaagtcaggc ccgtgggttc 3660
taccctcagt cccatcagga accagtaaaa catagacctt tacccaaagc aatggttgta 3720

```
gccaatggca acctggtgcc cactggaact gactcaggcc tgctgcctgt gggctcggag   3780

atcctggtag catcaagtct ggacgtgcag gccagagcca ccttcccaga caaggagcca   3840

acgccgcccc ccattacctc ctctcacttg ccttcccatt tcatgaaagg cgccatcatc   3900

cagctggcta cgggagagct gaagcgggtg gaggacctcc agacccagga ttttgtgcgc   3960

agtgccgaag tgagcggggg gctgaagatt gactctagca cggtcgtgga cattcaggag   4020

agccaatggc ctggatttgt catgctgcat tttgtggttg gtgagcagca gagcaaagtg   4080

agcatcgaag tgcccccga gcaccccttc tttgtatatg gccagggttg gtcctcttgc   4140

agccctgggc ggacgacaca actcttctct ctgccctgcc atcggctaca ggtgggagat   4200

gtctgcatct ctatcagttt acagagcttg aacagtaact cagtttctca ggccagctgt   4260

gctcccccaa gccagctggg tccccccga gaaaggcctg agaggacggt cttgggatcc   4320

agagagctat gtgacagtga ggggaagagc cagccggcag gagagggctc ccgtgtggta   4380

gagccttccc agcctgagtc cggtgctcag gcctgctggc cagccccgag cttccaaaga   4440

tacagcatgc aaggggagga ggcacgggct gcgctgctcc gtccctcttt cattccacag   4500

gaggtaaagc tgtccattga agggcgttcc aatgcgggaa aatgagattc tagccctcga   4560

ctgtgccttc tagttgccag ccatctgttg tttgcccctc ccccgtgcct tccttgaccc   4620

tggaaggtgc cactcccact gtcctttcct aataaaatga ggaaattgca tcgcattgtc   4680

tgagtaggtg tcattctatt ctggggggtg gggtggggca ggacagcaag ggggaggatt   4740

gggaagacaa tagcaggcat gctggggagt cgaccctgca aggtgagtgt aaagaacact   4800

agagcaaggc tacgtagata agtagcatgg cgggttaatc attaactaca aggaacccct   4860

agtgatggag ttggccactc cctctctgcg cgctcgctcg ctcactgagg ccgggcgacc   4920

aaaggtcgcc cgacgcccgg gctttgcccg ggcggcctca gtgagcgagc gagcgcgcag   4980

ctgcctgcag g                                                        4991
```

<210> SEQ ID NO 6
<211> LENGTH: 4899
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1364)..(1425)
<223> OTHER INFORMATION: hATXN1L non-coding exon 2
<220> FEATURE:
<221> NAME/KEY: misc_feature
<222> LOCATION: (1426)..(2266)
<223> OTHER INFORMATION: modified hATXN1L intron 2
<220> FEATURE:
<221> NAME/KEY: misc_feature
<222> LOCATION: (1770)..(1804)
<223> OTHER INFORMATION: miR30 5' flanking sequence
<220> FEATURE:
<221> NAME/KEY: misc_feature
<222> LOCATION: (1805)..(1889)
<223> OTHER INFORMATION: miS1
<220> FEATURE:
<221> NAME/KEY: misc_feature
<222> LOCATION: (1890)..(1931)
<223> OTHER INFORMATION: miR30 3' flanking sequence
<220> FEATURE:
<221> NAME/KEY: misc_feature
<222> LOCATION: (2267)..(2383)
<223> OTHER INFORMATION: hATXN1L non-coding exon 3
<220> FEATURE:
<221> NAME/KEY: misc_feature
<222> LOCATION: (2384)..(4453)
<223> OTHER INFORMATION: hATXN1L coding sequence
<220> FEATURE:
<221> NAME/KEY: misc_feature
<222> LOCATION: (4458)..(4677)
<223> OTHER INFORMATION: bGH polyA
<220> FEATURE:
<221> NAME/KEY: misc_feature
<222> LOCATION: (4759)..(4899)
<223> OTHER INFORMATION: AAV2 ITR

<400> SEQUENCE: 6
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
agtgaattcg tgaggctccg gtgcccgtca gtgggcagag cgcacatcgc ccacagtccc 240
cgagaagttg gggggagggg tcggcaattg aaccggtgcc tagagaaggt ggcgcggggt 300
aaactgggaa agtgatgtcg tgtactggct ccgccttttt cccgagggtg ggggagaacc 360
gtatataagt gcagtagtcg ccgtgaacgt tctttttcgc aacgggtttg ccgccagaac 420
acaggtaagt gccgtgtgtg gttcccgcgg gcctggcctc tttacgggtt atggcccttg 480
cgtgccttga attacttcca cctggctcca gtacgtgatt cttgatcccg agctggagcc 540
aggggcgggc cttgcgcttt aggagcccct tcgcctcgtg cttgagttga ggcctggcct 600
gggcgctggg gccgccgcgt gcgaatctgg tggcaccttc gcgcctgtct cgctgctttc 660
gataagtctc tagccattta aaatttttga tgacctgctg cgacgctttt tttctggcaa 720
gatagtcttg taaatgcggg ccaggatctg cacactggta tttcggtttt tgggcccgcg 780
gccggcgacg gggcccgtgc gtcccagcgc acatgttcgg cgaggcgggg cctgcgagcg 840
cggccaccga gaatcggacg ggggtagtct caagctggcc ggcctgctct ggtgcctggc 900
ctcgcgccgc cgtgtatcgc cccgccctgg gcggcaaggc tggcccggtc ggcaccagtt 960
gcgtgagcgg aaagatggcc gcttcccggc cctgctccag ggggctcaaa atggaggacg 1020
cggcgctcgg gagagcgggc gggtgagtca cccacacaaa ggaaaagggc ctttccgtcc 1080
tcagccgtcg cttcatgtga ctccacggag taccgggcgc cgtccaggca cctcgattag 1140
ttctggagct tttggagtac gtcgtcttta ggttgggggg aggggtttta tgcgatggag 1200
tttccccaca ctgagtgggt ggagactgaa gttaggccag cttggcactt gatgtaattc 1260
tcgttggaat ttgccctttt tgagtttgga tcttggttca ttctcaagcc tcagacagtg 1320
gttcaaagtt tttttcttcc atttcaggtg tcgtgaacac gtggctcccg agccagccgg 1380
gaggacactt actacagctg ctcagaagca ccactggaaa ctcaggtaat accggcactt 1440
tgaattcctt gtttcaggaa aatatctggg atgtcacagt ggaaaaacag aacagaatgt 1500
aatatagaaa gctcttttca gatccaaaga actggaacct ggttggaaga aataggcagc 1560
aaagttcatg tgcactgaag tgttcagacc aaaaagttgc tttataacaa tggacaaaag 1620
catttgtgaa aggtgacaat aagagaaaag ggaaagagaa ctttcttatg aatcatacag 1680
atacggggaa aaaaacaggc atgtttagag gaatggaacc agaatttcat ggagtggtgc 1740
ctggagcaga cttcgaaatt tcagctagcg cgtttagtga accgtcagat ggtaccgttt 1800
aaactcgagt gagcgcagca acgacctgaa gatcgatccg taaagccaca gatggggtcg 1860
atcttcaggt cgttgcttcg cctactagag cggccgccac agcggggaga tccagacatg 1920
ataagataca tacgcgtggc agaaaagaga caaggtgctt atgagacaca tgactaaccg 1980
tgaagctgtt ggtctccctg ggcttgtgga gcccacaggt tatttgtgca ttggtgaatg 2040
cgtgtccctg tagctctttg tgccttgtga tttccccgac tgtttctctc atgtcccagg 2100
ctggatgagt tgggggtagc ctccttgtct gccccttttct ctttcctcct tattttctaa 2160
cagtcccctt tgttacatct tcctccatgg cacagttctt tctatttcct ttgtcttggc 2220
tcatccctag gttacttttc tttgcctctg atttgttccc taatagatgt gggcgcccca 2280
gccagaagca gagaggggta cagggaagct acagagaagc cccttctgat gccccaggga 2340
gcaagtcgac tccttccagg ctccaggaac accacaaagc aatatgaaac ctgttcatga 2400
aaggagtcag gaatgccttc caccaaagaa acgagacctc cccgtgacca gcgaggatat 2460
ggggagaact accagctgct ccactaacca cacaccctcc agtgatgctt ctgaatggtc 2520
ccgaggggtt gtggtggctg ggcagagcca ggcaggagcc agagtcagcc tggggggtga 2580
tggagctgag gccatcaccg gtctgacagt ggaccagtat ggcatgctgt ataaggtggc 2640
tgtgccgcct gccacctttt caccaactgg actcccatct gtggtgaata tgagtccctt 2700
gcccccaacg tttaatgtag cgtcttcact aattcaacat ccaggcatcc actatcctcc 2760
actccactat gctcagctcc catccacctc gctgcagttc attgggtctc cttatagcct 2820
tccctatgct gtgccaccta atttcctacc gagtcccctc ctatctcctt ctgccaacct 2880
tgccacctct caccttccac actttgtgcc atatgcctca cttctggctg aaggagccac 2940
tcctccccca caggctccct ccccggccca ctcatttaac aaagctccct ctgccacctc 3000
cccatctggg caattgccac atcattcaag tactcagccg ctggaccttg ctccaggtcg 3060
gatgcccatt tattatcaga tgtccaggct acctgctggg tatactttgc atgaaacccc 3120
tccagcaggt gccagcccag ttcttacccc tcaggagagc cagtctgctc tggaagcagc 3180
tgctgcaaat ggaggacaga gaccacgaga gcgaaattta gtaagacggg aaagtgaagc 3240
ccttgactcc cccaacagca agggtgaagg ccagggactg gtgccagtgg tagaatgtgt 3300
ggtggatgga cagttgtttt caggttctca gactccacgg gtagaggtag cagcaccagc 3360
acaccggggg accccggaca ctgaccttga ggtccagcgg gtggttggcg ctttagcttc 3420
tcaggactat cgtgtggtgg cagctcagag gaaggaggaa cccagccccc tcaacctatc 3480
ccatcatacc cccgaccatc agggtgaggg gcgagggtca gccaggaacc ctgcagagct 3540
ggcagagaaa agtcaggccc gtgggttcta ccctcagtcc catcaggaac cagtaaaaca 3600
tagaccttta cccaaagcaa tggttgtagc caatggcaac ctggtgccca ctggaactga 3660
ctcaggcctg ctgcctgtgg gctcggagat cctggtagca tcaagtctgg acgtgcaggc 3720
cagagccacc ttcccagaca aggagccaac gccgcccccc attacctcct ctcacttgcc 3780
ttcccatttc atgaaaggcg ccatcatcca gctggctacg ggagagctga agcgggtgga 3840
ggacctccag acccaggatt ttgtgcgcag tgccgaagtg agcgggggggc tgaagattga 3900
ctctagcacg gtcgtggaca ttcaggagag ccaatggcct ggatttgtca tgctgcattt 3960
tgtggttggt gagcagcaga gcaaagtgag catcgaagtg ccccccgagc accccttctt 4020
tgtatatggc cagggttggt cctcttgcag ccctgggcgg acgacacaac tcttctctct 4080
gccctgccat cggctacagg tgggagatgt ctgcatctct atcagtttac agagcttgaa 4140
cagtaactca gtttctcagg ccagctgtgc tcccccaagc cagctgggtc ccccccgaga 4200

```
aaggcctgag aggacggtct tgggatccag agagctatgt gacagtgagg ggaagagcca   4260

gccggcagga gagggctccc gtgtggtaga gccttcccag cctgagtccg gtgctcaggc   4320

ctgctggcca gccccgagct tccaaagata cagcatgcaa ggggaggagg cacgggctgc   4380

gctgctccgt ccctctttca ttccacagga ggtaaagctg tccattgaag ggcgttccaa   4440

tgcgggaaaa tgagattcta gccctcgact gtgccttcta gttgccagcc atctgttgtt   4500

tgcccctccc ccgtgccttc cttgaccctg gaaggtgcca ctcccactgt cctttcctaa   4560

taaaatgagg aaattgcatc gcattgtctg agtaggtgtc attctattct ggggggtggg   4620

gtggggcagg acagcaaggg ggaggattgg gaagacaata gcaggcatgc tggggagtcg   4680

accctgcaag gtgagtgtaa agaacactag agcaaggcta cgtagataag tagcatggcg   4740

ggttaatcat taactacaag gaacccctag tgatggagtt ggccactccc tctctgcgcg   4800

ctcgctcgct cactgaggcc gggcgaccaa aggtcgcccg acgcccgggc tttgcccggg   4860

cggcctcagt gagcgagcga gcgcgcagct gcctgcagg                          4899
```

<210> SEQ ID NO 7
<211> LENGTH: 5066
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1364)..(1425)
<223> OTHER INFORMATION: hATXN1L non-coding exon 2
<220> FEATURE:
<221> NAME/KEY: misc_feature
<222> LOCATION: (1426)..(2433)
<223> OTHER INFORMATION: modified hATXN1L intron 2
<220> FEATURE:
<221> NAME/KEY: misc_feature
<222> LOCATION: (1754)..(1931)
<223> OTHER INFORMATION: miR128 promoter
<220> FEATURE:
<221> NAME/KEY: misc_feature
<222> LOCATION: (1937)..(1970)
<223> OTHER INFORMATION: miR30 5' flanking sequence
<220> FEATURE:
<221> NAME/KEY: misc_feature
<222> LOCATION: (1972)..(2056)
<223> OTHER INFORMATION: miS1
<220> FEATURE:
<221> NAME/KEY: misc_feature
<222> LOCATION: (2057)..(2098)
<223> OTHER INFORMATION: miR30 3' flanking sequence
<220> FEATURE:
<221> NAME/KEY: misc_feature
<222> LOCATION: (2434)..(2550)
<223> OTHER INFORMATION: hATXN1L non-coding exon 3
<220> FEATURE:
<221> NAME/KEY: misc_feature
<222> LOCATION: (2551)..(4620)
<223> OTHER INFORMATION: hATXN1L coding sequence
<220> FEATURE:
<221> NAME/KEY: misc_feature
<222> LOCATION: (4625)..(4844)
<223> OTHER INFORMATION: bGH polyA
<220> FEATURE:
<221> NAME/KEY: misc_feature
<222> LOCATION: (4926)..(5066)

-continued

<223> OTHER INFORMATION: AAV2 ITR

<400> SEQUENCE: 7

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
agtgaattcg tgaggctccg gtgcccgtca gtgggcagag cgcacatcgc ccacagtccc    240
cgagaagttg gggggagggg tcggcaattg aaccggtgcc tagagaaggt ggcgcggggt    300
aaactgggaa agtgatgtcg tgtactggct ccgccttttt cccgagggtg ggggagaacc    360
gtatataagt gcagtagtcg ccgtgaacgt tctttttcgc aacgggtttg ccgccagaac    420
acaggtaagt gccgtgtgtg gttcccgcgg gcctggcctc tttacgggtt atggcccttg    480
cgtgccttga attacttcca cctggctcca gtacgtgatt cttgatcccg agctggagcc    540
aggggcgggc cttgcgcttt aggagcccct tcgcctcgtg cttgagttga ggcctggcct    600
gggcgctggg gccgccgcgt gcgaatctgg tggcaccttc gcgcctgtct cgctgctttc    660
gataagtctc tagccattta aaatttttga tgacctgctg cgacgctttt tttctggcaa    720
gatagtcttg taaatgcggg ccaggatctg cacactggta tttcggtttt tgggcccgcg    780
gccggcgacg gggcccgtgc gtcccagcgc acatgttcgg cgaggcgggg cctgcgagcg    840
cggccaccga gaatcggacg ggggtagtct caagctggcc ggcctgctct ggtgcctggc    900
ctcgcgccgc cgtgtatcgc cccgccctgg gcggcaaggc tggcccggtc ggcaccagtt    960
gcgtgagcgg aaagatggcc gcttcccggc cctgctccag ggggctcaaa atggaggacg   1020
cggcgctcgg gagagcgggc gggtgagtca cccacacaaa ggaaaagggc ctttccgtcc   1080
tcagccgtcg cttcatgtga ctccacggag taccgggcgc cgtccaggca cctcgattag   1140
ttctggagct tttggagtac gtcgtcttta ggttgggggg aggggtttta tgcgatggag   1200
tttccccaca ctgagtgggt ggagactgaa gttaggccag cttggcactt gatgtaattc   1260
tcgttggaat ttgccctttt tgagtttgga tcttggttca ttctcaagcc tcagacagtg   1320
gttcaaagtt tttttcttcc atttcaggtg tcgtgaacac gtggctcccg agccagccgg   1380
gaggacactt actacagctg ctcagaagca ccactggaaa ctcaggtaat accggcactt   1440
tgaattcctt gtttcaggaa aatatctggg atgtcacagt ggaaaaacag aacagaatgt   1500
aatatagaaa gctcttttca gatccaaaga actggaacct ggttggaaga aataggcagc   1560
aaagttcatg tgcactgaag tgttcagacc aaaaagttgc tttataacaa tggacaaaag   1620
catttgtgaa aggtgacaat aagagaaaag ggaaagagaa ctttcttatg aatcatacag   1680
atacggggaa aaaaacaggc atgtttagag gaatggaacc agaatttcat ggagtggtgc   1740
ctggagcaga cttcgaagct tcctctgttc ttaaggctag ggaaccaaat taggttgttt   1800
caatatcgtg ctaaaagata ctgcctttag aagaaggcta ttgacaatcc agcgtgtctc   1860
ggtggaactc tgactccatg gttcactttc atgatggcca catgcctcct gcccagagcc   1920
cggcagccac gctagcgcgt ttagtgaacc gtcagatggt accgtttaaa ctcgagtgag   1980
cgcagcaacg acctgaagat cgatccgtaa agccacagat ggggtcgatc ttcaggtcgt   2040
tgcttcgcct actagagcgg ccgccacagc ggggagatcc agacatgata agatacatac   2100
gcgtggcaga aaagagacaa ggtgcttatg agacacatga ctaaccgtga agctgttggt   2160
ctccctgggc ttgtggagcc cacaggttat ttgtgcattg gtgaatgcgt gtccctgtag   2220
ctctttgtgc cttgtgattt ccccgactgt ttctctcatg tcccaggctg gatgagttgg   2280
```

```
gggtagcctc cttgtctgcc cctttctctt tcctccttat tttctaacag tcccctttgt   2340
tacatcttcc tccatggcac agttctttct atttcctttg tcttggctca tccctaggtt   2400
acttttcttt gcctctgatt tgttccctaa tagatgtggg cgccccagcc agaagcagag   2460
aggggtacag ggaagctaca gagaagcccc ttctgatgcc ccagggagca agtcgactcc   2520
ttccaggctc caggaacacc acaaagcaat atgaaacctg ttcatgaaag gagtcaggaa   2580
tgccttccac caaagaaacg agacctcccc gtgaccagcg aggatatggg gagaactacc   2640
agctgctcca ctaaccacac accctccagt gatgcttctg aatggtcccg aggggttgtg   2700
gtggctgggc agagccaggc aggagccaga gtcagcctgg ggggtgatgg agctgaggcc   2760
atcaccggtc tgacagtgga ccagtatggc atgctgtata aggtggctgt gccgcctgcc   2820
accttttcac caactggact cccatctgtg gtgaatatga gtcccttgcc cccaacgttt   2880
aatgtagcgt cttcactaat tcaacatcca ggcatccact atcctccact ccactatgct   2940
cagctcccat ccacctcgct gcagttcatt gggtctcctt atagccttcc ctatgctgtg   3000
ccacctaatt tcctaccgag tcccctccta tctccttctg ccaaccttgc cacctctcac   3060
cttccacact ttgtgccata tgcctcactt ctggctgaag gagccactcc tcccccacag   3120
gctccctccc cggcccactc atttaacaaa gctccctctg ccacctcccc atctgggcaa   3180
ttgccacatc attcaagtac tcagccgctg gaccttgctc caggtcggat gcccatttat   3240
tatcagatgt ccaggctacc tgctgggtat actttgcatg aaacccctcc agcaggtgcc   3300
agcccagttc ttacccctca ggagagccag tctgctctgg aagcagctgc tgcaaatgga   3360
ggacagagac cacgagagcg aaatttagta agacgggaaa gtgaagccct tgactccccc   3420
aacagcaagg gtgaaggcca gggactggtg ccagtggtag aatgtgtggt ggatggacag   3480
ttgttttcag gttctcagac tccacgggta gaggtagcag caccagcaca ccgggggacc   3540
ccggacactg accttgaggt ccagcgggtg gttggcgctt tagcttctca ggactatcgt   3600
gtggtggcag ctcagaggaa ggaggaaccc agcccctca acctatccca tcataccccc   3660
gaccatcagg gtgaggggcg agggtcagcc aggaaccctg cagagctggc agagaaaagt   3720
caggcccgtg ggttctaccc tcagtcccat caggaaccag taaaacatag acctttaccc   3780
aaagcaatgg ttgtagccaa tggcaacctg gtgcccactg gaactgactc aggcctgctg   3840
cctgtgggct cggagatcct ggtagcatca agtctggacg tgcaggccag agccaccttc   3900
ccagacaagg agccaacgcc gccccccatt acctcctctc acttgccttc ccatttcatg   3960
aaaggcgcca tcatccagct ggctacggga gagctgaagc gggtggagga cctccagacc   4020
caggattttg tgcgcagtgc cgaagtgagc ggggggctga agattgactc tagcacggtc   4080
gtggacattc aggagagcca atggcctgga tttgtcatgc tgcattttgt ggttggtgag   4140
cagcagagca aagtgagcat cgaagtgccc cccgagcacc ccttctttgt atatggccag   4200
ggttggtcct cttgcagccc tgggcggacg acacaactct tctctctgcc ctgccatcgg   4260
ctacaggtgg gagatgtctg catctctatc agtttacaga gcttgaacag taactcagtt   4320
tctcaggcca gctgtgctcc cccaagccag ctgggtcccc cccgagaaag gcctgagagg   4380
acggtcttgg gatccagaga gctatgtgac agtgagggga agagccagcc ggcaggagag   4440
ggctcccgtg tggtagagcc ttcccagcct gagtccggtg ctcaggcctg ctggccagcc   4500
ccgagcttcc aaagatacag catgcaaggg gaggaggcac gggctgcgct gctccgtccc   4560
tctttcattc cacaggaggt aaagctgtcc attgaagggc gttccaatgc gggaaaatga   4620
```

gattctagcc ctcgactgtg ccttctagtt gccagccatc tgttgtttgc ccctcccccg 4680
tgccttcctt gaccctggaa ggtgccactc ccactgtcct ttcctaataa aatgaggaaa 4740
ttgcatcgca ttgtctgagt aggtgtcatt ctattctggg gggtggggtg gggcaggaca 4800
gcaaggggga ggattgggaa gacaatagca ggcatgctgg ggagtcgacc ctgcaaggtg 4860
agtgtaaaga acactagagc aaggctacgt agataagtag catggcgggt taatcattaa 4920
ctacaaggaa cccctagtga tggagttggc cactccctct ctgcgcgctc gctcgctcac 4980
tgaggccggg cgaccaaagg tcgcccgacg cccgggcttt gcccgggcgg cctcagtgag 5040
cgagcgagcg cgcagctgcc tgcagg 5066

<210> SEQ ID NO 8
<211> LENGTH: 2179
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(130)
<223> OTHER INFORMATION: AAV2 ITR
<220> FEATURE:
<221> NAME/KEY: misc_feature
<222> LOCATION: (194)..(1356)
<223> OTHER INFORMATION: EF1a promoter
<220> FEATURE:
<221> NAME/KEY: misc_feature
<222> LOCATION: (1471)..(1504)
<223> OTHER INFORMATION: miR30 5' flanking sequence
<220> FEATURE:
<221> NAME/KEY: misc_feature
<222> LOCATION: (1473)..(1956)
<223> OTHER INFORMATION: bGH polyA
<220> FEATURE:
<221> NAME/KEY: misc_feature
<222> LOCATION: (1506)..(1590)
<223> OTHER INFORMATION: miS1
<220> FEATURE:
<221> NAME/KEY: misc_feature
<222> LOCATION: (1591)..(1632)
<223> OTHER INFORMATION: miR30 3' flanking sequence
<220> FEATURE:
<221> NAME/KEY: misc_feature
<222> LOCATION: (2039)..(2179)
<223> OTHER INFORMATION: AAV2 ITR

<400> SEQUENCE: 8
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
agtgaattcg tgaggctccg gtgcccgtca gtgggcagag cgcacatcgc ccacagtccc 240
cgagaagttg gggggagggg tcggcaattg aaccggtgcc tagagaaggt ggcgcggggt 300
aaactgggaa agtgatgtcg tgtactggct ccgccttttt cccgagggtg ggggagaacc 360
gtatataagt gcagtagtcg ccgtgaacgt tctttttcgc aacgggtttg ccgccagaac 420
acaggtaagt gccgtgtgtg gttcccgcgg gcctggcctc tttacgggtt atggcccttg 480
cgtgccttga attacttcca cctggctcca gtacgtgatt cttgatcccg agctggagcc 540
aggggcgggc cttgcgcttt aggagcccct tcgcctcgtg cttgagttga ggcctggcct 600
gggcgctggg gccgccgcgt gcgaatctgg tggcaccttc gcgcctgtct cgctgctttc 660
gataagtctc tagccattta aaatttttga tgacctgctg cgacgctttt tttctggcaa 720
gatagtcttg taaatgcggg ccaggatctg cacactggta tttcggtttt tgggcccgcg 780

-continued

```
gccggcgacg gggcccgtgc gtcccagcgc acatgttcgg cgaggcgggg cctgcgagcg    840

cggccaccga gaatcggacg ggggtagtct caagctggcc ggcctgctct ggtgcctggc    900

ctcgcgccgc cgtgtatcgc cccgccctgg gcggcaaggc tggcccggtc ggcaccagtt    960

gcgtgagcgg aaagatggcc gcttcccggc cctgctccag ggggctcaaa atggaggacg   1020

cggcgctcgg gagagcgggc gggtgagtca cccacacaaa ggaaaagggc ctttccgtcc   1080

tcagccgtcg cttcatgtga ctccacggag taccgggcgc cgtccaggca cctcgattag   1140

ttctggagct tttggagtac gtcgtcttta ggttgggggg aggggtttta tgcgatggag   1200

tttccccaca ctgagtgggt ggagactgaa gttaggccag cttggcactt gatgtaattc   1260

tcgttggaat ttgccctttt tgagtttgga tcttggttca ttctcaagcc tcagacagtg   1320

gttcaaagtt tttttcttcc atttcaggtg tcgtgaacac ctagaacctc ttccccagac   1380

caggactggg gctttacccc agagcctcgc ctcgccgccg tgagcaggca gaggatttgc   1440

acacgccgag cagggaatgg ctttgctagc gcgtttagtg aaccgtcaga tggtaccgtt   1500

taaactcgag tgagcgcagc aacgacctga agatcgatcc gtaaagccac agatggggtc   1560

gatcttcagg tcgttgcttc gcctactaga gcggccgcca cagcggggag atccagacat   1620

gataagatac atacgcgttg gcagtgagat ttggggggaaa ggggaggcat gaagtcagcc   1680

tcccaaggca ggatctgttg ttcattaccc catggcatcc tttcaggaca accccagagc   1740

tccctcgact gtgccttcta gttgccagcc atctgttgtt tgcccctccc ccgtgccttc   1800

cttgaccctg gaaggtgcca ctcccactgt cctttcctaa taaaatgagg aaattgcatc   1860

gcattgtctg agtaggtgtc attctattct ggggggtggg gtggggcagg acagcaaggg   1920

ggaggattgg gaagacaata gcaggcatgc tggggagtcg accctgcaag gtgagtgtaa   1980

agaacactag agcaaggcta cgtagataag tagcatggcg ggttaatcat taactacaag   2040

gaacccctag tgatggagtt ggccactccc tctctgcgcg ctcgctcgct cactgaggcc   2100

gggcgaccaa aggtcgcccg acgcccgggc tttgcccggg cggcctcagt gagcgagcga   2160

gcgcgcagct gcctgcagg                                                2179
```

COMBINED TRANSGENE AND INTRON-DERIVED MIRNA THERAPY FOR TREATMENT OF SCA1

REFERENCE TO RELATED APPLICATIONS

The present application is a national phase application under 35 U.S.C. § 371 of International Application No. PCT/US2020/046499, filed Aug. 14, 2020, which claims the priority benefit of U.S. provisional application No. 62/887,209, filed Aug. 15, 2019, the entire contents of each of which is incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Jan. 28, 2022, is named CHOPP0036US_ST25.txt and is 46.4 kilobytes in size.

BACKGROUND

1. Field

The present disclosure relates generally to the fields of molecular biology and medicine. More particularly, it concerns nucleic acids expressing both a therapeutic protein and a therapeutic inhibitory RNA in addition to methods of using such nucleic acids in the treatment of disease.

2. Description of Related Art

Spinocerebellar ataxia 1 (SCA1) is one of nine polyglutamine (polyQ) expansion diseases and is characterized by cerebellar ataxia and neuronal degeneration in the cerebellum and brainstem. It is caused by an unstable CAG expansion in the ATXN1 gene, which encodes the ataxin-1 protein (Banfi et al., 1994; Orr et al., 1993). Ataxin-1 is ubiquitously expressed and is prevalent in cerebellar Purkinje cells (Servadio et al., 1995). Post-necropsy analysis of patient cerebellar tissues identified ataxin-1 positive nuclear inclusions in affected Purkinje cells and brainstem neurons, but also in unaffected neurons of the cerebrum (Currier et al., 1972, Jackson et al., 1977).

In unaffected humans, there are 6-42 CAG repeats interspersed with 1-3 CATs in ATXN1, which are histidine-encoding codons. In SCA1 patients, the CAG repeat expansion in ATXN1 is expanded to more than 39 repeats, causing an expanded polyglutamine (polyQ) stretch in the ataxin1 protein. The disease-causing mutation acts through a toxic gain of function mechanism, and suppressing its expression is expected to not only arrest disease progression, but also reverse disease phenotypes (Keiser et al., 2014; Keiser et al., 2013; Keiser et al., 2016; Oz et al., 2014; Oz et al., 2011; Xia et al., 2004; Zu et al., 2004). However, there are currently no effective treatment strategies for this disease.

SUMMARY

In one embodiment, provided herein are nucleic acid molecules comprising a first expression cassette encoding human Ataxin-1-like (hAtxn1L) and a second expression cassette encoding an inhibitory RNA targeting human ataxin-1 mRNA. In some aspects, the second expression cassette encoding an inhibitory RNA targeting human ataxin-1 mRNA is present within an intron of the first expression cassette encoding human Ataxin-1-like (hAtxn1L). In some aspects, the intron is flanked on its 5' end by a non-coding exon 2 of hATXN1L having a sequence at least 90%, 91%, 92%, 93%, 94%, 95%, 96%, 97%, 98%, or 99% identical to nucleotides 1364-1425 of SEQ ID NO: 7. In some aspects, the intron is flanked on its 5' end by a non-coding exon 2 of hATXN1L having a sequence identical to nucleotides 1364-1425 of SEQ ID NO: 7. In some aspects, the intron is flanked on its 3' end by a non-coding exon 3 of hATXN1L having a sequence at least 90%, 91%, 92%, 93%, 94%, 95%, 96%, 97%, 98%, or 99% identical to nucleotides 2434-2550 of SEQ ID NO: 7. In some aspects, the intron is flanked on its 3' end by a non-coding exon 3 of hATXN1L having a sequence identical to nucleotides 2434-2550 of SEQ ID NO: 7.

In some aspects, the inhibitory RNA is a siRNA, shRNA, or miRNA. In some aspects, the inhibitory RNA is a miRNA. In some aspects, the miRNA comprises the sequence of SEQ ID NO: 1. In some aspects, the miRNA comprises a sequence having at least 90%, 91%, 92%, 93%, 94%, 95%, 96%, 97%, 98%, or 99% identity to SEQ ID NO: 1. In some aspects, the miRNA may be flanked by the flanking sequences of a human miRNA. In some aspects, the miRNA may be flanked by the flanking sequences of miR30. In some aspects, the miRNA may be flanked on its 5' end by a miR30 5' flanking sequence having at least 90%, 91%, 92%, 93%, 94%, 95%, 96%, 97%, 98%, or 99% identity to nucleotides 1937-1970 of SEQ ID NO: 7. In some aspects, the miRNA may be flanked on its 5' end by a miR30 5' flanking sequence identical to nucleotides 1937-1970 of SEQ ID NO: 7. In some aspects, the miRNA may be flanked on its 3" end by a miR30 3' flanking sequence having at least 90%, 91%, 92%, 93%, 94%, 95%, 96%, 97%, 98%, or 99% identity to nucleotides 2057-2098 of SEQ ID NO: 7. In some aspects, the miRNA may be flanked on its 3' end by a miR30 3' flanking sequence identical to nucleotides 2057-2098 of SEQ ID NO: 7.

In some aspects, the second expression cassette encoding the inhibitory RNA comprises a promoter that is operably linked to the inhibitory RNA coding sequence. In some aspects, the promoter is a constitutive promoter, a cell-type specific promoter, or an inducible promoter. In some aspects, the promoter is a pol III promoter or a U6 promoter. In some aspects, the promoter is a promoter for a miRNA expressed in the brain. In some aspects, the promoter is a miR128 promoter. In some aspects, the promoter has a sequence at least 90%, 95%, 97%, 98%, or 99% identical to the sequence of nucleotides 1754-1931 of SEQ ID NO: 7. In some aspects, the promoter has a sequence identical to the sequence of nucleotides 1754-1931 of SEQ ID NO: 7.

In aspects where the second expression cassette encoding an inhibitory RNA targeting human ataxin-1 mRNA is present within an intron of the first expression cassette encoding human Ataxin-1-like (hAtxn1L), the inhibitory RNA may not be operably linked to a promoter.

In some aspects, the first expression cassette encoding hAtxn1L comprises a promoter that is operably linked to the hAtxn1L coding sequence. In some aspects, the promoter is a constitutive promoter, a cell-type specific promoter, or an inducible promoter. In some aspects, the promoter has a sequence at least 90%, 95%, 97%, 98%, or 99% identical to the sequence of nucleotides 194-1356 of SEQ ID NO: 7. In some aspects, the promoter has a sequence identical to the sequence of nucleotides 194-1356 of SEQ ID NO: 7.

In some aspects, the first and/or second expression cassette comprises an enhancer element. In some aspects, the first and/or second expression cassette comprises an intron, a filler polynucleotide sequence, poly A signal, or a combination thereof.

In one embodiment, provided herein are cells comprising a nucleic acid of any one of the present embodiments.

In one embodiment, provided herein are recombinant adeno-associated virus (rAAV) vectors comprising an AAV capsid protein and nucleic acid molecule of any one of the present embodiments. In some aspects, the AAV vectors comprise an AAV particle comprising AAV capsid proteins, and wherein the first and/or second expression cassette is inserted between a pair of AAV inverted terminal repeats (ITRs). In some aspects, the AAV capsid proteins are derived from or selected from the group consisting of AAV1, AAV2, AAV3, AAV4, AAV5, AAV6, AAV7, AAV8, AAV9, AAV10, AAV11, AAV12, AAV-rh74, AAV-rh10, and AAV-2i8 VP1, VP2 and/or VP3 capsid proteins, or a capsid protein having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 VP1, VP2 and/or VP3 capsid proteins. In some aspects, the pair of AAV ITRs is derived from, comprises or consists of an AAV1, AAV2, AAV3, AAV4, AAV5, AAV6, AAV7, AAV8, AAV9, AAV10, AAV11, AAV12, AAV-rh74, AAV-rh10 or AAV-2i8 ITR, or an ITR having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 ITR sequence.

In one embodiment, provided herein are methods of treating spinocerebellar ataxia (SCA) type 1 in a patient in need thereof, the method comprising administering to the patient a first expression cassette encoding human Ataxin-1-like (hAtxn1L) and a second expression cassette encoding an inhibitory RNA targeting human ataxin-1 mRNA. In some aspects, the first expression cassette encoding human Ataxin-1-like (hAtxn1L) and the second expression cassette encoding an inhibitory RNA targeting human ataxin-1 mRNA are both present on the same nucleic acid molecule. In some aspects, the second expression cassette encoding an inhibitory RNA targeting human ataxin-1 mRNA is present within an intron of the first expression cassette encoding human Ataxin-1-like (hAtxn1L). In some aspects, the intron is flanked on its 5' end by a non-coding exon 2 of hATXN1L having a sequence at least 90%, 91%, 92%, 93%, 94%, 95%, 96%, 97%, 98%, or 99% identical to nucleotides 1364-1425 of SEQ ID NO: 7. In some aspects, the intron is flanked on its 5' end by a non-coding exon 2 of hATXN1L having a sequence identical to nucleotides 1364-1425 of SEQ ID NO: 7. In some aspects, the intron is flanked on its 3' end by a non-coding exon 3 of hATXN1L having a sequence at least 90%, 91%, 92%, 93%, 94%, 95%, 96%, 97%, 98%, or 99% identical to nucleotides 2434-2550 of SEQ ID NO: 7. In some aspects, the intron is flanked on its 3' end by a non-coding exon 3 of hATXN1L having a sequence identical to nucleotides 2434-2550 of SEQ ID NO: 7.

In some aspects, the inhibitory RNA is a siRNA, shRNA, or miRNA. In some aspects, the inhibitory RNA is a miRNA. In some aspects, the miRNA comprises the sequence of SEQ ID NO: 1. In some aspects, the miRNA comprises a sequence having at least 90%, 91%, 92%, 93%, 94%, 95%, 96%, 97%, 98%, or 99% identity to SEQ ID NO: 1. In some aspects, the miRNA may be flanked by the flanking sequences of a human miRNA. In some aspects, the miRNA may be flanked by the flanking sequences of miR30. In some aspects, the miRNA may be flanked on its 5' end by a miR30 5' flanking sequence having at least 90%, 91%, 92%, 93%, 94%, 95%, 96%, 97%, 98%, or 99% identity to nucleotides 1937-1970 of SEQ ID NO: 7. In some aspects, the miRNA may be flanked on its 5' end by a miR30 5' flanking sequence identical to nucleotides 1937-1970 of SEQ ID NO: 7. In some aspects, the miRNA may be flanked on its 3" end by a miR30 3' flanking sequence having at least 90%, 91%, 92%, 93%, 94%, 95%, 96%, 97%, 98%, or 99% identity to nucleotides 2057-2098 of SEQ ID NO: 7. In some aspects, the miRNA may be flanked on its 3' end by a miR30 3' flanking sequence identical to nucleotides 2057-2098 of SEQ ID NO: 7. In some aspects, the inhibitory RNA decreases expression of human Ataxin-1.

In some aspects, the second expression cassette encoding the inhibitory RNA comprises a promoter that is operably linked to the inhibitory RNA coding sequence. In some aspects, the promoter is a constitutive promoter, a cell-type specific promoter, or an inducible promoter. In some aspects, the promoter is a pol III promoter or a U6 promoter. In some aspects, the promoter is a promoter for a miRNA expressed in the brain. In some aspects, the promoter is a miR128 promoter. In some aspects, the promoter has a sequence at least 90%, 95%, 97%, 98%, or 99% identical to the sequence of nucleotides 1754-1931 of SEQ ID NO: 7. In some aspects, the promoter has a sequence identical to the sequence of nucleotides 1754-1931 of SEQ ID NO: 7.

In aspects where the second expression cassette encoding an inhibitory RNA targeting human ataxin-1 mRNA is present within an intron of the first expression cassette encoding human Ataxin-1-like (hAtxn1L), the inhibitory RNA may not be operably linked to a promoter.

In some aspects, the first expression cassette encoding hAtxn1L comprises a promoter that is operably linked to the hAtxn1L coding sequence. In some aspects, the promoter is a constitutive promoter, a cell-type specific promoter, or an inducible promoter. In some aspects, the promoter has a sequence at least 90%, 95%, 97%, 98%, or 99% identical to the sequence of nucleotides 194-1356 of SEQ ID NO: 7. In some aspects, the promoter has a sequence identical to the sequence of nucleotides 194-1356 of SEQ ID NO: 7.

In some aspects, the first and/or second expression cassette comprises an enhancer element. In some aspects, the first and/or second expression cassette comprises an intron, a filler polynucleotide sequence, poly A signal, or a combination thereof.

In some aspects, the methods reduce expression of ataxin-1. In some aspects, the methods reduce the level of Atxn1 mRNA by at least 10% in the cerebellum, deep cerebellar nuclei, brain stem, and/or thalamus. In some aspects, the methods reduce the level of Atxn1 mRNA by at least 10%-50% in the cerebellum, deep cerebellar nuclei, brain stem, and/or thalamus.

In some aspects, the first and/or second expression cassette is comprised in a viral vector. In some aspects, the viral vector is selected from an adeno-associated viral (AAV) vector, a lentiviral vector, or a retroviral vector. In some aspects, the AAV vector comprises an AAV particle comprising AAV capsid proteins, and wherein the first and/or second expression cassette is inserted between a pair of AAV inverted terminal repeats (ITRs). In some aspects, the AAV capsid proteins are derived from or selected from the group consisting of AAV1, AAV2, AAV3, AAV4, AAV5, AAV6, AAV7, AAV8, AAV9, AAV10, AAV11, AAV12, AAV-rh74, AAV-rh10, and AAV-2i8 VP1, VP2 and/or VP3 capsid proteins, or a capsid protein having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 VP1, VP2 and/or VP3 capsid proteins. In some aspects, the pair of AAV ITRs is derived from, comprises or consists of an AAV1, AAV2, AAV3, AAV4, AAV5, AAV6, AAV7, AAV8, AAV9, AAV10, AAV11, AAV12, AAV-rh74, AAV-rh10 or AAV-2i8 ITR, or an ITR having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 ITR sequence.

In some aspects, a plurality of the viral vectors are administered. In some aspects, the viral vectors are administered at a dose of about $1\times10^{6}$ to about $1\times10^{18}$ vector genomes per kilogram (vg/kg). In some aspects, the viral vectors are administered at a dose from about $1\times10^{7}$-$1\times10^{17}$, about $1\times10^{8}$-$1\times10^{16}$, about $1\times10^{9}$-$1\times10^{15}$, about $1\times10^{10}$-$1\times10^{14}$, about $1\times10^{10}$-$1\times10^{13}$, about $1\times10^{10}$-$1\times10^{13}$, about $1\times10^{10}$-$1\times10^{11}$, about $1\times10^{11}$-$1\times10^{12}$, about $1\times10^{12}$-$\times10^{13}$, or about $1\times10^{13}$-$1\times10^{14}$ vg/kg of the patient. In some aspects, the viral vectors are administered at a dose of about 0.5-4 ml of $1\times10^{6}$-$1\times10^{16}$ vg/ml.

In some aspects, the methods further comprise administering a plurality of empty viral capsids. In some aspects, the empty viral capsids are formulated with the viral particles administered to the patient. In some aspects, the empty viral capsids are administered or formulated with 1.0 to 100-fold excess of viral vector particles or empty viral capsids. In some aspects, the empty viral capsids are administered or formulated with 1.0 to 100-fold excess of viral vector particles to empty viral capsids. In some aspects, the empty viral capsids are administered or formulated with about 1.0 to 100-fold excess of empty viral capsids to viral vector particles.

In some aspects, the administration is to the central nervous system. In some aspects, the administration is to the brain. In some aspects, the administration is to a cisterna magna, an intraventricular space, an ependyma, a brain ventricle, a subarachnoid space, and/or an intrathecal space. In some aspects, the brain ventricle is the rostral lateral ventricle, and/or the caudal lateral ventricle, and/or the right lateral ventricle, and/or the left lateral ventricle, and/or the right rostral lateral ventricle, and/or the left rostral lateral ventricle, and/or the right caudal lateral ventricle, and/or the left caudal lateral ventricle. In some aspects, the administering comprises intraventricular injection and/or intraparenchymal injection. In some aspects, ependymal cells, pial cells, endothelial cells, brain ventricle cells, meningeal cells, glial cells and/or neurons express the inhibitory RNA and/or the human Ataxin-1-like protein.

In some aspects, the administration is at a single location in the brain. In some aspects, the administration is at 1-5 locations in the brain.

In some aspects, the method reduces an adverse symptom of spinocerebellar ataxia (SCA) type 1. In some aspects, the adverse symptom comprises an early stage or late stage symptom; a behavior, personality or language symptom; a motor function symptom; and/or a cognitive symptom. In some aspects, the method increases, improves, preserves, restores or rescues memory deficits, memory defects or cognitive function of the patient. In some aspects, the method improves or inhibits or reduces or prevents worsening of loss of coordination, slow movement or body stiffness. In some aspects, the method improves or inhibits or reduces or prevents worsening of spasms or fidgety movements. In some aspects, the method improves or inhibits or reduces or prevents worsening of depression or irritability. In some aspects, the method improves or inhibits or reduces or prevents worsening of dropping items, falling, losing balance, difficulty speaking or difficulty swallowing. In some aspects, the method improves or inhibits or reduces or prevents worsening of ability to organize. In some aspects, the method improves or inhibits or reduces or prevents worsening of ataxia or diminished reflexes. In some aspects, the method improves or inhibits or reduces or prevents worsening of seizures or tremors seizures or tremors.

In some aspects, the patient is a human.

In some aspects, the methods further comprise administering one or more immunosuppressive agents. In some aspects, the immunosuppressive agent is administered prior to or contemporaneously with administration of the expression cassettes. In some aspects, the immunosuppressive agent is an anti-inflammatory agent.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows construct cartoons of hATXN1L under the control of an EF1α promoter; hATXN1L having an intron and under the control of an EF1α promoter; hATXN1L having an intron that includes miR128 and under the control of an EF1α promoter; and hATXN1L having an intron that includes miR128 along with miR128 promoter and under the control of an EF1α promoter. FIG. 1B shows splicing of the constructs when transiently transfected into HEK293 cells. FIG. 1C shows miR128 expression as a mature miRNA from the constructs. FIG. 1D shows expression of hATXN1L from the constructs.

FIGS. 2A-D. Expression of miS1 from hATXN1L intron 2. FIG. 2A shows construct cartoons of hATXN1L under the control of an EF1α promoter; hATXN1L having an intron and under the control of an EF1α promoter; hATXN1L having an intron that includes miS1 and under the control of an EF1α promoter; hATXN1L having an intron that includes miS1 along with the miR128 promoter and under the control of an EF1α promoter; and miS1 directly under the control of the EF1α promoter. FIG. 2B shows miS1 expression from the constructs. FIG. 2C shows hATXN1L expression from the constructs. FIG. 2D shows hATXN1 levels following transfection with the constructs.

FIGS. 3A-B. Construct cartoon. FIG. 3A show the EF1α promoter driving human Ataxin-1-like between two Inverted Terminal Repeats (ITR) as a control vector. FIG. 3B shows the murine U6 promoter driving miRNA, miS1, followed by the EF1α promoter driving human Ataxin-1-like. A control guide virus will also be tested.

FIG. 5A shows 12-week-old baseline rotarod performance over 4 days. See FIG. 5B for a legend. FIG. 5B shows rotarod performance at 20 weeks of age (8 weeks post-injection). FIG. 5C shows the difference in rotarod performance at 20 weeks versus 12 weeks for each experimental group. *p<0.05; p<0.005; *p<0.001, based on two-way ANOVA followed by Dunnett's Multiple Comparisons post hoc analysis.

FIG. 6A shows qRT-PCR for miS1 levels.

FIG. 6B shows qRT-PCR for human ATXN1 mRNA levels. FIG. 6C shows qRT-PCR for human ATXN1L mRNA levels. Samples were obtained from 20-week-old mice, 8 weeks post-injection. *p<0.001; **p<0.0001, relative to Saline, based on one-way ANOVA followed by Dunnett's Multiple Comparisons post hoc analysis.

FIG. 7A shows qRT-PCR for mouse Vegfa mRNA levels. FIG. 7B shows qRT-PCR for mouse Grm1 mRNA levels. Samples were obtained from 20-week-old mice, 8 weeks post-injection. ****p<0.0001, relative to wild-type, based on one-way ANOVA followed by Dunnett's Multiple Comparisons post hoc analysis.

FIG. 8A shows qRT-PCR for mouse Gfap mRNA levels. FIG. 8B shows qRT-PCR for mouse Iba1 mRNA levels. *p<0.05; p<0.01; *p<0.001; ****p<0.0001, relative to Saline, based on one-way ANOVA followed by Dunnett's Multiple Comparisons post hoc analysis.

FIG. 10A shows qRT-PCR for miS1 expression. FIG. 10B shows qRT-PCR for human ATXN1 mRNA levels. FIG. 10C shows qRT-PCR for human ATXN1L mRNA levels. FIG. 10D shows miS1 expression relative to human ATXN1L mRNA levels. FIG. 10E shows qRT-PCR for mouse Gfap mRNA levels. FIG. 10F shows qRT-PCR for mouse Iba1 mRNA levels. *p<0.05 relative to no injection. n=4-6 for all groups.

DETAILED DESCRIPTION

Figure 1A:
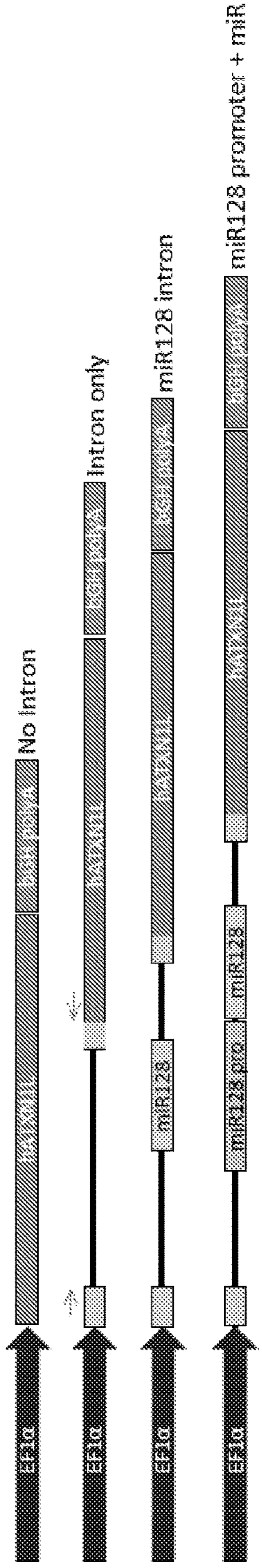
FIGS. 1A-D. Expression of miR128 from hATXN1L intron 2.

Animal studies have been pivotal to better define the cellular and molecular mechanisms underlying SCA1 pathogenesis (Bowman et al., 2007; Cvetanovic et al., 2007; Lai et al., 2011; Lam et al., 2006; Lambrechts & Carmeliet, 2006; Lim et al., 2008; Morrison, 2009; Orr, 2012; Rodriguez-Lebron et al., 2013; Serra et al., 2004; Serra et al., 2006; Tsuda et al., 2005; Zoghbi & Orr, 2009). This gain of function disease benefits from approaches to reduce the expression of the disease allele. For example, a doxycycline-inducible transgenic mouse model for SCA1 demonstrated that repressing mutant protein production 12 weeks after sustained expression significantly improved pathology and behavior deficits (Zu et al., 2004).

RNA interference (RNAi) is a naturally occurring process that mediates gene silencing and is currently being investigated as therapy for dominant diseases, such as SCA1. RNAi therapy by non-allele specific silencing of ataxin-1 mRNA provides therapeutic benefit in symptomatic SCA1 mice (Keiser et al., 2013, which is incorporated herein by reference in its entirety for all purposes). In addition, delivery of adeno-associated viral (AAV) vectors encoding a microRNA (miRNA) targeting ataxin-1 (miS1) to symptomatic SCA1 transgenic mouse cerebellum at 12 weeks of age reversed neuropathological and motor phenotypes in a dose dependent fashion by 20 weeks of age (Keiser et al., 2016; U.S. Pat. Appln. Publn. US 2018/0169269; U.S. Pat. Appln. Publn. US 2019/0071671; each of which is incorporated herein by reference in its entirety for all purposes). However, at the highest doses, treatment resulted in almost complete ablation of human ataxin-1 by qPCR, but no improvement in motor phenotypes or neuropathology. Moreover, the highest doses were associated with toxicity. The source of the toxicity for the highest doses were suspected to be i) too much viral capsid, ii) inhibition of the endogenous RNAi pathway in cells from high expression of miS1, or iii) a combination of these two factors. Two miRNAs are dysregulated in SCA1 mouse models: miR-124a is decreased, and miR150 is increased, and earlier work at an RNAi dose of 1E9 showed recovery of the miR150 levels and its target (Adlakha & Saini, 2014; Rodriguez-Lebron et al., 2013). Mice receiving the highest doses of AAV.miS1 (2.6E10 and 8E10 vg) showed reduced miR-124a and miR-150 expression, suggesting saturation of the endogenous RNAi machinery. Finally, in mice injected with empty capsids only, at levels mirroring the highest doses, there was enhanced microglial and astroglial activation. Together these studies support that efforts to reduce viral load, as well as levels of artificial miRNA expression, should be explored. While altering promoters for RNAi is one method to accomplish this (Boudreau et al., 2009), methods to further improve the therapeutic window are needed.

As an alternative to the RNAi methods, exogenous overexpression of human ataxin-1-like by AAV-delivery prevented disease phenotypes and demonstrated neuroprotective effects in B05 transgenic SCA1 mice to a similar extent as knocking down ataxin-1 by RNAi (Keiser et al., 2013). Modulation of the disease through gene overexpression of an ataxin-1-like transgenic allele has also been demonstrated to improve disease phenotypes in SCA1 knock-in mice (154Q) (Bowman et al., 2007). The mechanism for therapy based on ATXN1L overexpression is that ataxin-1-like, ataxin-1 and mutant, polyQ-expanded ataxin-1 all interact with *Capicua* through their AXH domain (Lam et al., 2006; Lim et al., 2008). Interestingly, ATXN1L does not have a polyQ region but if overexpressed in vitro, can effectively compete with the disease-inducing interactions between mutant ataxin-1 and *Capicua* (Bowman et al., 2007).

Provided herein are single constructs that provide for expression of both a gene silencing sequence (e.g., a miRNA) for suppressing the expression of a disease protein (e.g., toxic mutant ataxin-1) and overexpression of a protein that provides disease protective effects (e.g., ataxin-1-like). Also provided are methods of using such constructs to provide combinatorial therapeutic benefit at lower doses, thereby reducing the need for high viral delivery and the associated toxicity.

One construct provided herein is hATXN1L having an intron that includes miR128 and under the control of an EF1α promoter as provided in SEQ ID NO: 4. One construct provided herein is hATXN1L having an intron that includes miR128 along with miR128 promoter and under the control of an EF1α promoter as provided in SEQ ID NO: 5. One construct provided herein is hATXN1L having an intron that includes miS1 and under the control of an EF1α promoter as provided in SEQ ID NO: 6. One construct provided herein is hATXN1L having an intron that includes miS1 along with the miR128 promoter and under the control of an EF1α promoter as provided in SEQ ID NO: 7.

I. INHIBITORY RNAs

"RNA interference (RNAi)" is the process of sequence-specific, post-transcriptional gene silencing initiated by siRNA. During RNAi, siRNA induces degradation of target mRNA with consequent sequence-specific inhibition of gene expression.

An "inhibitory RNA," "RNAi," "small interfering RNA" or "short interfering RNA" or "siRNA" molecule, "short hairpin RNA" or "shRNA" molecule, or "miRNA" is an RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong polIII-based promoters. Many shRNAs have demonstrated effective knock down of the target sequences in vitro as well as in vivo, however, some shRNAs which demonstrated effective knock down of the target gene were also found to have toxicity in vivo.

miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). See U.S. Pat. No. 10,093,927, which is incorporated by reference.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A siRNA target generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. Any gene being expressed in a cell can be targeted. Preferably, a target gene is one involved in or associated with the progression of cellular activities important to disease or of particular interest as a research object.

II. METHODS OF ADMINISTRATION

Any suitable cell or mammal can be administered or treated by a method or use described herein. Typically, a mammal is in need of a method described herein, that is suspected of having or expressing an abnormal or aberrant protein that is associated with a disease state.

Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. In certain embodiments a mammal is a non-rodent mammal (e.g., human, pig, goat, sheep, horse, dog, or the like). In certain embodiments a non-rodent mammal is a human. A mammal can be any age or at any stage of development (e.g., an adult, teen, child, infant, or a mammal in utero). A mammal can be male or female. In certain embodiments a mammal can be an animal disease model, for example, animal models having or expressing an abnormal or aberrant protein that is associated with a disease state or animal models with insufficient expression of a protein, which causes a disease state.

Mammals (subjects) treated by a method or composition described herein include adults (18 years or older) and children (less than 18 years of age). Adults include the elderly. Representative adults are 50 years or older. Children range in age from 1-2 years old, or from 2-4, 4-6, 6-18, 8-10, 10-12, 12-15 and 15-18 years old. Children also include infants. Infants typically range from 1-12 months of age.

In certain embodiments, a method includes administering a plurality of viral particles or nanoparticles to a mammal as set forth herein, where severity, frequency, progression or time of onset of one or more symptoms of a disease state, such as a neuro-degenerative disease, decreased, reduced, prevented, inhibited or delayed. In certain embodiments, a method includes administering a plurality of viral particles or nanoparticles to a mammal to treat an adverse symptom of a disease state, such as a neuro-degenerative disease. In certain embodiments, a method includes administering a plurality of viral particles or nanoparticles to a mammal to stabilize, delay or prevent worsening, or progression, or reverse and adverse symptom of a disease state, such as a neuro-degenerative disease.

In certain embodiments a method includes administering a plurality of viral particles or nanoparticles to the central nervous system, or portion thereof as set forth herein, of a mammal and severity, frequency, progression or time of onset of one or more symptoms of a disease state, such as a neuro-degenerative disease, are decreased, reduced, prevented, inhibited or delayed by at least about 5 to about 10, about 10 to about 25, about 25 to about 50, or about 50 to about 100 days.

In certain embodiments, a symptom or adverse effect comprises an early stage, middle or late stage symptom; a behavior, personality or language symptom; swallowing, movement, seizure, tremor or fidgeting symptom; ataxia; and/or a cognitive symptom such as memory, ability to organize.

In some embodiments, viral and non-viral based gene transfer methods can be used to introduce nucleic acids in mammalian cells or target tissues. Such methods can be used to administer nucleic acids encoding inhibitory RNAs and/or therapeutic proteins to cells in culture or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, 1992; Nabel & Feigner, 1993; Mitani & Caskey, 1993; Dillon, 1993; Miller, 1992; Van Brunt, 1988; Vigne, 1995; Kremer & Perricaudet, 1995; Haddada et al., 1995; and Yu et al., 1994.

Methods of non-viral delivery of nucleic acids include exosomes, lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in (e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91117424; WO 91116024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

The term "vector" refers to small carrier nucleic acid molecule, a plasmid, virus (e.g., AAV vector, retroviral vector, lentiviral vector), or other vehicle that can be manipulated by insertion or incorporation of a nucleic acid. Vectors, such as viral vectors, can be used to introduce/transfer nucleic acid sequences into cells, such that the nucleic acid sequence therein is transcribed and, if encoding a protein, subsequently translated by the cells.

An "expression vector" is a specialized vector that contains a gene or nucleic acid sequence with the necessary regulatory regions needed for expression in a host cell. An expression vector may contain at least an origin of replication for propagation in a cell and optionally additional elements, such as a heterologous nucleic acid sequence, expression control element (e.g., a promoter, enhancer), intron, ITR(s), and polyadenylation signal.

A viral vector is derived from or based upon one or more nucleic acid elements that comprise a viral genome. Exemplary viral vectors include adeno-associated virus (AAV) vectors, retroviral vectors, and lentiviral vectors.

The term "recombinant," as a modifier of vector, such as recombinant viral, e.g., lenti- or parvo-virus (e.g., AAV) vectors, as well as a modifier of sequences such as recombinant nucleic acid sequences and polypeptides, means that the compositions have been manipulated (i.e., engineered) in a fashion that generally does not occur in nature. A particular example of a recombinant vector, such as an AAV, retroviral, or lentiviral vector would be where a nucleic acid sequence that is not normally present in the wild-type viral genome is inserted within the viral genome. An example of a recombinant nucleic acid sequence would be where a nucleic acid (e.g., gene) encodes an inhibitory RNA cloned into a vector, with or without 5', 3' and/or intron regions that the gene is normally associated within the viral genome. Although the term "recombinant" is not always used herein in reference to vectors, such as viral vectors, as well as sequences such as polynucleotides, "recombinant" forms including nucleic acid sequences, polynucleotides, transgenes, etc. are expressly included in spite of any such omission.

A recombinant viral "vector" is derived from the wild type genome of a virus, such as AAV, retrovirus, or lentivirus, by using molecular methods to remove the wild type genome from the virus, and replacing with a non-native nucleic acid, such as a nucleic acid sequence. Typically, for example, for AAV, one or both inverted terminal repeat (ITR) sequences of the AAV genome are retained in the recombinant AAV vector. A "recombinant" viral vector (e.g., rAAV) is distinguished from a viral (e.g., AAV) genome, since all or a part of the viral genome has been replaced with a non-native sequence with respect to the viral genomic nucleic acid such a nucleic acid encoding a transactivator or nucleic acid encoding an inhibitory RNA or nucleic acid encoding a therapeutic protein. Incorporation of such non-native nucleic acid sequences therefore defines the viral vector as a "recombinant" vector, which in the case of AAV can be referred to as a "rAAV vector."

A. Adeno-Associated Virus

Adeno-associated virus (AAV) is a small nonpathogenic virus of the parvoviridae family. To date, numerous serologically distinct AAVs have been identified, and more than a dozen have been isolated from humans or primates. AAV is distinct from other members of this family by its dependence upon a helper virus for replication.

AAV genomes can exist in an extrachromosomal state without integrating into host cellular genomes; possess a broad host range; transduce both dividing and non-dividing cells in vitro and in vivo and maintain high levels of expression of the transduced genes. AAV viral particles are heat stable; resistant to solvents, detergents, changes in pH, and temperature; and can be column purified and/or concentrated on CsCl gradients or by other means. The AAV genome comprises a single-stranded deoxyribonucleic acid (ssDNA), either positive- or negative-sensed. The approximately 5 kb genome of AAV consists of one segment of single stranded DNA of either plus or minus polarity. The ends of the genome are short inverted terminal repeats (ITRs) that can fold into hairpin structures and serve as the origin of viral DNA replication.

An AAV "genome" refers to a recombinant nucleic acid sequence that is ultimately packaged or encapsulated to form an AAV particle. An AAV particle often comprises an AAV genome packaged with AAV capsid proteins. In cases where recombinant plasmids are used to construct or manufacture recombinant vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsulated into viral particles. Thus, an AAV vector "genome" refers to nucleic acid that is packaged or encapsulated by AAV capsid proteins.

The AAV virion (particle) is a non-enveloped, icosahedral particle approximately 25 nm in diameter. The AAV particle comprises an icosahedral symmetry comprised of three related capsid proteins, VP1, VP2 and VP3, which interact together to form the capsid. The right ORF often encodes the capsid proteins VP1, VP2, and VP3. These proteins are often found in a ratio of 1:1:10 respectively, but may be in varied ratios, and are all derived from the right-hand ORF. The VP1, VP2 and VP3 capsid proteins differ from each other by the use of alternative splicing and an unusual start codon. Deletion analysis has shown that removal or alteration of VP1 which is translated from an alternatively spliced message results in a reduced yield of infectious particles. Mutations within the VP3 coding region result in the failure to produce any single-stranded progeny DNA or infectious particles.

An AAV particle is a viral particle comprising an AAV capsid. In certain embodiments, the genome of an AAV particle encodes one, two or all VP1, VP2 and VP3 polypeptides.

The genome of most native AAVs often contain two open reading frames (ORFs), sometimes referred to as a left ORF and a right ORE. The left ORF often encodes the non-structural Rep proteins, Rep 40, Rep 52, Rep 68 and Rep 78, which are involved in regulation of replication and transcription in addition to the production of single-stranded progeny genomes. Two of the Rep proteins have been associated with the preferential integration of AAV genomes into a region of the q arm of human chromosome 19. Rep68/78 have been shown to possess NTP binding activity as well as DNA and RNA helicase activities. Some Rep proteins possess a nuclear localization signal as well as several potential phosphorylation sites. In certain embodiments the genome of an AAV (e.g., an rAAV) encodes some or all of the Rep proteins. In certain embodiments the genome of an AAV (e.g., an rAAV) does not encode the Rep proteins. In certain embodiments one or more of the Rep proteins can be delivered in trans and are therefore not included in an AAV particle comprising a nucleic acid encoding a polypeptide.

The ends of the AAV genome comprise short inverted terminal repeats (ITR) which have the potential to fold into T-shaped hairpin structures that serve as the origin of viral DNA replication. Accordingly, the genome of an AAV comprises one or more (e.g., a pair of) ITR sequences that flank a single stranded viral DNA genome. The ITR sequences often have a length of about 145 bases each. Within the ITR region, two elements have been described which are believed to be central to the function of the ITR, a GAGC repeat motif and the terminal resolution site (trs). The repeat motif has been shown to bind Rep when the ITR is in either a linear or hairpin conformation. This binding is thought to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

In certain embodiments, an AAV (e.g., a rAAV) comprises two ITRs. In certain embodiments, an AAV (e.g., a rAAV) comprises a pair of ITRs. In certain embodiments, an AAV (e.g., a rAAV) comprises a pair of ITRs that flank (i.e., are at each 5' and 3' end) of a nucleic acid sequence that at least encodes a polypeptide having function or activity.

An AAV vector (e.g., rAAV vector) can be packaged and is referred to herein as an "AAV particle" for subsequent infection (transduction) of a cell, ex vivo, in vitro or in vivo. Where a recombinant AAV vector is encapsulated or packaged into an AAV particle, the particle can also be referred to as a "rAAV particle." In certain embodiments, an AAV particle is a rAAV particle. A rAAV particle often comprises a rAAV vector, or a portion thereof. A rAAV particle can be one or more rAAV particles (e.g., a plurality of AAV particles). rAAV particles typically comprise proteins that encapsulate or package the rAAV vector genome (e.g., capsid proteins). It is noted that reference to a rAAV vector can also be used to reference a rAAV particle.

Any suitable AAV particle (e.g., rAAV particle) can be used for a method or use herein. A rAAV particle, and/or genome comprised therein, can be derived from any suitable serotype or strain of AAV. A rAAV particle, and/or genome comprised therein, can be derived from two or more serotypes or strains of AAV. Accordingly, a rAAV can comprise proteins and/or nucleic acids, or portions thereof, of any serotype or strain of AAV, wherein the AAV particle is suitable for infection and/or transduction of a mammalian cell. Non-limiting examples of AAV serotypes include AAV1, AAV2, AAV3, AAV4, AAV5, AAV6, AAV7, AAV8, AAV9, AAV10, AAV11, AAV12, AAV-rh74, AAV-rh10 and AAV-2i8.

In certain embodiments a plurality of rAAV particles comprises particles of, or derived from, the same strain or serotype (or subgroup or variant). In certain embodiments a plurality of rAAV particles comprise a mixture of two or more different rAAV particles (e.g., of different serotypes and/or strains).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

In certain embodiments, a rAAV particle excludes certain serotypes. In one embodiment, a rAAV particle is not an AAV4 particle. In certain embodiments, a rAAV particle is antigenically or immunologically distinct from AAV4. Distinctness can be determined by standard methods. For example, ELISA and Western blots can be used to determine whether a viral particle is antigenically or immunologically distinct from AAV4. Furthermore, in certain embodiments a rAAV2 particle retains tissue tropism distinct from AAV4.

In certain embodiments, a rAAV vector based upon a first serotype genome corresponds to the serotype of one or more of the capsid proteins that package the vector. For example, the serotype of one or more AAV nucleic acids (e.g., ITRs) that comprises the AAV vector genome corresponds to the serotype of a capsid that comprises the rAAV particle.

In certain embodiments, a rAAV vector genome can be based upon an AAV (e.g., AAV2) serotype genome distinct from the serotype of one or more of the AAV capsid proteins that package the vector. For example, a rAAV vector genome can comprise AAV2 derived nucleic acids (e.g., ITRs), whereas at least one or more of the three capsid proteins are derived from a different serotype, e.g., an AAV1, AAV3, AAV4, AAV5, AAV6, AAV7, AAV8, AAV9, AAV10, AAV11, AAV12, Rh10, Rh74 or AAV-2i8 serotype or variant thereof.

In certain embodiments, a rAAV particle or a vector genome thereof related to a reference serotype has a polynucleotide, polypeptide or subsequence thereof that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a polynucleotide, polypeptide or subsequence of an AAV1, AAV2, AAV3, AAV4, AAV5, AAV6, AAV7, AAV8, AAV9, AAV10, AAV11, AAV12, Rh10, Rh74 or AAV-2i8 particle. In particular embodiments, a rAAV particle or a vector genome thereof related to a reference serotype has a capsid or ITR sequence that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a capsid or ITR sequence of an AAV1, AAV2, AAV3, AAV4, AAV5, AAV6, AAV7, AAV8, AAV9, AAV10, AAV11, AAV12, Rh10, Rh74 or AAV-2i8 serotype.

In certain embodiments, a method herein comprises use, administration or delivery of a rAAV1, rAAV2, rAAV3, rAAV4, rAAV5, rAAV6, rAAV7, rAAV8, rAAV9, rAAV10, rAAV11, rAAV12, rRh10, rRh74 or rAAV-2i8 particle.

In certain embodiments, a method herein comprises use, administration or delivery of a rAAV2 particle. In certain embodiments a rAAV2 particle comprises an AAV2 capsid. In certain embodiments a rAAV2 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments a rAAV2 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments, a rAAV2 particle is a variant of a native or wild-type AAV2 particle. In some aspects, one or more capsid proteins of an AAV2 variant have 1, 2, 3, 4, 5, 5-10, 10-15, 15-20 or more amino acid substitutions compared to capsid protein(s) of a native or wild-type AAV2 particle.

In certain embodiments a rAAV9 particle comprises an AAV9 capsid. In certain embodiments a rAAV9 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments a rAAV9 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments, a rAAV9 particle is a variant of a native or wild-type AAV9 particle. In some aspects, one or more capsid proteins of an AAV9 variant have 1, 2, 3, 4, 5, 5-10, 10-15, 15-20 or more amino acid substitutions compared to capsid protein(s) of a native or wild-type AAV9 particle.

In certain embodiments, a rAAV particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV1, AAV2, AAV3, AAV4, AAV5, AAV6, AAV7, AAV8, AAV9, AAV10, AAV11, AAV12, AAV-rh74, AAV-rh10 or AAV-2i8, as long as they retain one or more desired ITR functions (e.g., ability to form a hairpin, which allows DNA replication; integration of the AAV DNA into a host cell genome; and/or packaging, if desired).

In certain embodiments, a rAAV2 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

In certain embodiments, a rAAV9 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

A rAAV particle can comprise an ITR having any suitable number of "GAGC" repeats. In certain embodiments an ITR of an AAV2 particle comprises 1, 2, 3, 4, 5, 6, 7, 8, 9 or 10 or more "GAGC" repeats. In certain embodiments a rAAV2 particle comprises an ITR comprising three "GAGC" repeats. In certain embodiments a rAAV2 particle comprises an ITR which has less than four "GAGC" repeats. In certain embodiments a rAAV2 particle comprises an ITR which has more than four "GAGC" repeats. In certain embodiments an ITR of a rAAV2 particle comprises a Rep binding site wherein the fourth nucleotide in the first two "GAGC" repeats is a C rather than a T.

Exemplary suitable length of DNA can be incorporated in rAAV vectors for packaging/encapsidation into a rAAV particle can about 5 kilobases (kb) or less. In particular, embodiments, length of DNA is less than about 5 kb, less than about 4.5 kb, less than about 4 kb, less than about 3.5 kb, less than about 3 kb, or less than about 2.5 kb.

rAAV vectors that include a nucleic acid sequence that directs the expression of an RNAi or polypeptide can be generated using suitable recombinant techniques known in the art (e.g., see Sambrook et al., 1989). Recombinant AAV vectors are typically packaged into transduction-competent AAV particles and propagated using an AAV viral packaging system. A transduction-competent AAV particle is capable of binding to and entering a mammalian cell and subsequently delivering a nucleic acid cargo (e.g., a heterologous gene) to the nucleus of the cell. Thus, an intact rAAV particle that is transduction-competent is configured to transduce a mammalian cell. A rAAV particle configured to transduce a mammalian cell is often not replication competent, and requires additional protein machinery to self-replicate. Thus, a rAAV particle that is configured to transduce a mammalian cell is engineered to bind and enter a mammalian cell and deliver a nucleic acid to the cell, wherein the nucleic acid for delivery is often positioned between a pair of AAV ITRs in the rAAV genome.

Suitable host cells for producing transduction-competent AAV particles include but are not limited to microorganisms, yeast cells, insect cells, and mammalian cells that can be, or have been, used as recipients of a heterologous rAAV vectors. Cells from the stable human cell line, HEK293 (readily available through, e.g., the American Type Culture Collection under Accession Number ATCC CRL1573) can be used. In certain embodiments a modified human embryonic kidney cell line (e.g., HEK293), which is transformed with adenovirus type-5 DNA fragments, and expresses the adenoviral E1a and E1b genes is used to generate recombinant AAV particles. The modified HEK293 cell line is readily transfected, and provides a particularly convenient platform in which to produce rAAV particles. Methods of generating high titer AAV particles capable of transducing mammalian cells are known in the art. For example, AAV particle can be made as set forth in Wright, 2008 and Wright, 2009.

In certain embodiments, AAV helper functions are introduced into the host cell by transfecting the host cell with an AAV helper construct either prior to, or concurrently with, the transfection of an AAV expression vector. AAV helper constructs are thus sometimes used to provide at least transient expression of AAV rep and/or cap genes to complement missing AAV functions necessary for productive AAV transduction. AAV helper constructs often lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors are known which encode Rep and/or Cap expression products.

B. Retrovirus

Viral vectors for use as a delivered agent in the methods, compositions and uses herein include a retroviral vector (see e.g., Miller (1992) *Nature,* 357:455-460). Retroviral vectors are well suited for delivering nucleic acid into cells because of their ability to deliver an unrearranged, single copy gene into a broad range of rodent, primate and human somatic cells. Retroviral vectors integrate into the genome of host cells. Unlike other viral vectors, they only infect dividing cells.

Retroviruses are RNA viruses such that the viral genome is RNA. When a host cell is infected with a retrovirus, the genomic RNA is reverse transcribed into a DNA intermediate, which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences permitting encapsulation without coincident production of a contaminating helper virus. A helper virus is not required for the production of the recombinant retrovirus if the sequences for encapsulation are provided by co-transfection with appropriate vectors.

The retroviral genome and the proviral DNA have three genes: the gag, the pol and the env, which are flanked by two long terminal repeat (LTR) sequences. The gag gene encodes the internal structural (matrix, capsid, and nucleocapsid) proteins and the env gene encodes viral envelope glycoproteins. The pol gene encodes products that include the RNA-directed DNA polymerase reverse transcriptase that transcribes the viral RNA into double-stranded DNA, integrase that integrate the DNA produced by reverse transcriptase into host chromosomal DNA, and protease that acts to process the encoded gag and pol genes. The 5' and 3' LTRs serve to promote transcription and polyadenylation of the virion RNAs. The LTR contains all other cis-acting sequences necessary for viral replication.

Retroviral vectors are described by Coffin et al., *Retroviruses*, Cold Spring Harbor Laboratory Press (1997). Exemplary of a retrovirus is Moloney murine leukemia virus (MMLV) or the murine stem cell virus (MSCV). Retroviral vectors can be replication-competent or replication-defective. Typically, a retroviral vector is replication-defective in which the coding regions for genes necessary for additional rounds of virion replication and packaging are deleted or replaced with other genes. Consequently, the viruses are not able to continue their typical lytic pathway once an initial target cell is infected. Such retroviral vectors, and the necessary agents to produce such viruses (e.g., packaging cell line) are commercially available (see, e.g., retroviral vectors and systems available from Clontech, such as Catalog number 634401, 631503, 631501, and others, Clontech, Mountain View, Calif.).

Such retroviral vectors can be produced as delivered agents by replacing the viral genes required for replication with the nucleic acid molecule to be delivered. The resulting genome contains an LTR at each end with the desired gene or genes in between. Methods of producing retrovirus are known to one of skill in the art (see, e.g., International published PCT Application No. WO1995/026411). The retroviral vector can be produced in a packaging cell line containing a helper plasmid or plasmids. The packaging cell line provides the viral proteins required for capsid production and the virion maturation of the vector (e.g., gag, pol and env genes). Typically, at least two separate helper plasmids (separately containing the gag and pol genes; and the env gene) are used so that recombination between the vector plasmid cannot occur. For example, the retroviral vector can be transferred into a packaging cell line using standard methods of transfection, such as calcium phosphate mediated transfection. Packaging cell lines are well known to one of skill in the art, and are commercially available. An exemplary packaging cell line is GP2-293 packaging cell line (Catalog Numbers 631505, 631507, 631512, Clontech). After sufficient time for virion product, the virus is harvested. If desired, the harvested virus can be used to infect a second packaging cell line, for example, to produce a virus with varied host tropism. The end result is a replicative incompetent recombinant retrovirus that includes the nucleic acid of interest but lacks the other structural genes such that a new virus cannot be formed in the host cell.

References illustrating the use of retroviral vectors in gene therapy include: Clowes et al., (1994) *J. Clin. Invest.* 93:644-651; Kiem et al., (1994) *Blood* 83:1467-1473; Salmons and Gunzberg (1993) *Human Gene Therapy* 4:129-141; Grossman and Wilson (1993) *Curr. Opin. in Genetics and Devel.* 3:110-114; Sheridan (2011) *Nature Biotechnology,* 29:121; Cassani et al. (2009) *Blood,* 114:3546-3556.

C. Lentivirus

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif vpr, vpu and nef are deleted making the vector biologically safe. Lentiviral vectors are well known in the art (see, e.g., U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell, wherein a suitable host cell is transfected with two or more vectors carrying the packaging functions, namely gag, pol and env, as well as rev and tat, is described in U.S. Pat. No. 5,994,136, incorporated herein by reference.

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

D. Other Viral Vectors

The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

E. Chimeric Viral Vectors

Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 2000) and adenoviral/adeno-associated viral vectors (Fisher et al., 1996; U.S. Pat. No. 5,871,982) have been described. These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

III. PHARMACEUTICAL COMPOSITIONS

As used herein the term "pharmaceutically acceptable" and "physiologically acceptable" mean a biologically acceptable composition, formulation, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Such composition, "pharmaceutically acceptable" and "physiologically acceptable" formulations and compositions can be sterile. Such pharmaceutical formulations and compositions may be used, for example in administering a viral particle or nanoparticle to a subject.

Such formulations and compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Supplementary active compounds (e.g., preservatives, antibacterial, antiviral and antifungal agents) can also be incorporated into the formulations and compositions.

Pharmaceutical compositions typically contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as surfactants, wetting or emulsifying agents, pH buffering substances, and the like, may be present in such vehicles.

Pharmaceutical compositions can be formulated to be compatible with a particular route of administration or delivery, as set forth herein or known to one of skill in the art. Thus, pharmaceutical compositions include carriers, diluents, or excipients suitable for administration or delivery by various routes.

Pharmaceutical forms suitable for injection or infusion of viral particles or nanoparticles can include sterile aqueous solutions or dispersions which are adapted for the extemporaneous preparation of sterile injectable or infusible solutions or dispersions, optionally encapsulated in liposomes. In all cases, the ultimate form should be a sterile fluid and stable under the conditions of manufacture, use and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Isotonic agents, for example, sugars, buffers or salts (e.g., sodium chloride) can be included. Prolonged absorption of injectable compositions can be brought about by the use in the compositions of agents delaying absorption, for example, aluminum monostearate and gelatin.

Solutions or suspensions of viral particles or nanoparticles can optionally include one or more of the following components: a sterile diluent such as water for injection, saline solution, such as phosphate buffered saline (PBS), artificial CSF, a surfactants, fixed oils, a polyol (for example, glycerol, propylene glycol, and liquid polyethylene glycol, and the like), glycerin, or other synthetic solvents; antibacterial and antifungal agents such as parabens, chlorobutanol, phenol, ascorbic acid, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical formulations, compositions and delivery systems appropriate for the compositions, methods and uses of the invention are known in the art (see, e.g., Remington: The Science and Practice of Pharmacy (2003) $20^{th}$ ed., Mack Publishing Co., Easton, PA; Remington's Pharmaceutical Sciences (1990) $18^{th}$ ed., Mack Publishing Co., Easton, PA; The Merck Index (1996) $12^{th}$ ed., Merck Publishing Group, Whitehouse, NJ; Pharmaceutical Principles of Solid Dosage Forms (1993), Technonic Publishing Co., Inc., Lancaster, Pa.; Ansel and Stoklosa, Pharmaceutical Calculations (2001) $11^{th}$ ed., Lippincott Williams & Wilkins, Baltimore, MD; and Poznansky et al., Drug Delivery Systems (1980), R. L. Juliano, ed., Oxford, N.Y., pp. 253-315).

Viral particles and their compositions may be formulated in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms are dependent upon the number of viral particles or nanoparticles believed necessary to produce the desired effect(s). The amount necessary can be formulated in a single dose, or can be formulated in multiple dosage units. The dose may be adjusted to a suitable viral particle or nanoparticle concentration, optionally combined with an anti-inflammatory agent, and packaged for use.

In one embodiment, pharmaceutical compositions will include sufficient genetic material to provide a therapeutically effective amount, i.e., an amount sufficient to reduce or ameliorate symptoms or an adverse effect of a disease state in question or an amount sufficient to confer the desired benefit.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Thus, for example, viral particles, nanoparticles, and pharmaceutical compositions thereof can be packaged in single or multiple unit dosage form for ease of administration and uniformity of dosage.

Formulations containing viral particles or nanoparticles typically contain an effective amount, the effective amount being readily determined by one skilled in the art. The viral particles or nanoparticles may typically range from about 1% to about 95% (w/w) of the composition, or even higher if suitable. The quantity to be administered depends upon factors such as the age, weight and physical condition of the mammal or the human subject considered for treatment. Effective dosages can be established by one of ordinary skill in the art through routine trials establishing dose response curves.

IV. DEFINITIONS

The terms “polynucleotide,” “nucleic acid” and “transgene” are used interchangeably herein to refer to all forms of nucleic acid, oligonucleotides, including deoxyribonucleic acid (DNA) and ribonucleic acid (RNA) and polymers thereof. Polynucleotides include genomic DNA, cDNA and antisense DNA, and spliced or unspliced mRNA, rRNA, tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides can include naturally occurring, synthetic, and intentionally modified or altered polynucleotides (e.g., variant nucleic acid). Polynucleotides can be single stranded, double stranded, or triplex, linear or circular, and can be of any suitable length. In discussing polynucleotides, a sequence or structure of a particular polynucleotide may be described herein according to the convention of providing the sequence in the 5' to 3' direction.

A nucleic acid encoding a polypeptide often comprises an open reading frame that encodes the polypeptide. Unless otherwise indicated, a particular nucleic acid sequence also includes degenerate codon substitutions.

Nucleic acids can include one or more expression control or regulatory elements operably linked to the open reading frame, where the one or more regulatory elements are configured to direct the transcription and translation of the polypeptide encoded by the open reading frame in a mammalian cell. Non-limiting examples of expression control/regulatory elements include transcription initiation sequences (e.g., promoters, enhancers, a TATA box, and the like), translation initiation sequences, mRNA stability sequences, poly A sequences, secretory sequences, and the like. Expression control/regulatory elements can be obtained from the genome of any suitable organism.

A “promoter” refers to a nucleotide sequence, usually upstream (5') of a coding sequence, which directs and/or controls the expression of the coding sequence by providing the recognition for RNA polymerase and other factors required for proper transcription. A pol II promoter includes a minimal promoter that is a short DNA sequence comprised of a TATA-box and optionally other sequences that serve to specify the site of transcription initiation, to which regulatory elements are added for control of expression. A type 1 pol III promoter includes three cis-acting sequence elements downstream of the transcriptional start site: a) 5'sequence element (A block); b) an intermediate sequence element (I block); c) 3' sequence element (C block). A type 2 pol III promoter includes two essential cis-acting sequence elements downstream of the transcription start site: a) an A box (5' sequence element); and b) a B box (3' sequence element). A type 3 pol III promoter includes several cis-acting promoter elements upstream of the transcription start site, such as a traditional TATA box, proximal sequence element (PSE), and a distal sequence element (DSE).

An “enhancer” is a DNA sequence that can stimulate transcription activity and may be an innate element of the promoter or a heterologous element that enhances the level or tissue specificity of expression. It is capable of operating in either orientation (5'->3' or 3'->5'), and may be capable of functioning even when positioned either upstream or downstream of the promoter.

Promoters and/or enhancers may be derived in their entirety from a native gene, or be composed of different elements derived from different elements found in nature, or even be comprised of synthetic DNA segments. A promoter or enhancer may comprise DNA sequences that are involved in the binding of protein factors that modulate/control effectiveness of transcription initiation in response to stimuli, physiological or developmental conditions.

Non-limiting examples of promoters include SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Exemplary constitutive promoters include the promoters for the following genes which encode certain constitutive or “housekeeping” functions: hypoxanthine phosphoribosyl transferase (HPRT), dihydrofolate reductase (DHFR), adenosine deaminase, phosphoglycerol kinase (PGK), pyruvate kinase, phosphoglycerol mutase, actin promoter, U6, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others. In addition, sequences derived from intronic miRNA promoters, such as, for example, the miR107, miR206, miR208b, miR548f-2, miR569, miR590, miR566, and miR128 promoter, will also find use herein (see, e.g., Monteys et al., 2010). Accordingly, any of the above-referenced constitutive promoters can be used to control transcription of a heterologous gene insert.

A “transgene” is used herein to conveniently refer to a nucleic acid sequence/polynucleotide that is intended or has been introduced into a cell or organism. Transgenes include any nucleic acid, such as a gene that encodes an inhibitory RNA or polypeptide or protein, and are generally heterologous with respect to naturally occurring AAV genomic sequences.

The term “transduce” refers to introduction of a nucleic acid sequence into a cell or host organism by way of a vector (e.g., a viral particle). Introduction of a transgene into a cell by a viral particle is can therefore be referred to as “transduction” of the cell. The transgene may or may not be integrated into genomic nucleic acid of a transduced cell. If an introduced transgene becomes integrated into the nucleic acid (genomic DNA) of the recipient cell or organism it can be stably maintained in that cell or organism and further passed on to or inherited by progeny cells or organisms of the recipient cell or organism. Finally, the introduced transgene may exist in the recipient cell or host organism extra chromosomally, or only transiently. A “transduced cell” is therefore a cell into which the transgene has been introduced by way of transduction. Thus, a "transduced" cell is a cell into which, or a progeny thereof in which a transgene has been introduced. A transduced cell can be propagated, transgene transcribed and the encoded inhibitory RNA or protein expressed. For gene therapy uses and methods, a transduced cell can be in a mammal.

Transgenes under control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting a suitable promoter (constitutive versus inducible; strong versus weak), it is possible to control both the existence and level of expression of a polypeptide in the genetically modified cell. If the gene encoding the polypeptide is under the control of an inducible promoter, delivery of the polypeptide in situ is triggered by exposing the genetically modified cell in situ to conditions for permitting transcription of the polypeptide, e.g., by intraperitoneal injection of specific inducers of the inducible promoters which control transcription of the agent. For example, in situ expression by genetically modified cells of a polypeptide encoded by a gene under the control of the metallothionein promoter, is enhanced by contacting the genetically modified cells with a solution containing the appropriate (i.e., inducing) metal ions in situ.

A nucleic acid/transgene is "operably linked" when it is placed into a functional relationship with another nucleic acid sequence. A nucleic acid/transgene encoding and RNAi or a polypeptide, or a nucleic acid directing expression of a polypeptide may include an inducible promoter, or a tissue-specific promoter for controlling transcription of the encoded polypeptide. A nucleic acid operably linked to an expression control element can also be referred to as an expression cassette.

In certain embodiments, CNS-specific or inducible promoters, enhancers and the like, are employed in the methods and uses described herein. Non-limiting examples of CNS-specific promoters include those isolated from the genes from myelin basic protein (MBP), glial fibrillary acid protein (GFAP), and neuron specific enolase (NSE). Non-limiting examples of inducible promoters include DNA responsive elements for ecdysone, tetracycline, hypoxia and IFN.

In certain embodiments, an expression control element comprises a CMV enhancer. In certain embodiments, an expression control element comprises a beta actin promoter. In certain embodiments, an expression control element comprises a chicken beta actin promoter. In certain embodiments, an expression control element comprises a CMV enhancer and a chicken beta actin promoter.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular type of variant is a mutant protein, which refers to a protein encoded by a gene having a mutation, e.g., a missense or nonsense mutation.

A "nucleic acid" or "polynucleotide" variant refers to a modified sequence which has been genetically altered compared to wild-type. The sequence may be genetically modified without altering the encoded protein sequence. Alternatively, the sequence may be genetically modified to encode a variant protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of a protein encoded thereby, and some codons of the nucleic acid variant will be changed which in turn changes the amino acids of a protein encoded thereby.

The terms "protein" and "polypeptide" are used interchangeably herein. The "polypeptides" encoded by a "nucleic acid" or "polynucleotide" or "transgene" disclosed herein include partial or full-length native sequences, as with naturally occurring wild-type and functional polymorphic proteins, functional subsequences (fragments) thereof, and sequence variants thereof, so long as the polypeptide retains some degree of function or activity. Accordingly, in methods and uses of the invention, such polypeptides encoded by nucleic acid sequences are not required to be identical to the endogenous protein that is defective, or whose activity, function, or expression is insufficient, deficient or absent in a treated mammal.

Non-limiting examples of modifications include one or more nucleotide or amino acid substitutions (e.g., about 1 to about 3, about 3 to about 5, about 5 to about 10, about 10 to about 15, about 15 to about 20, about 20 to about 25, about 25 to about 30, about 30 to about 40, about 40 to about 50, about 50 to about 100, about 100 to about 150, about 150 to about 200, about 200 to about 250, about 250 to about 500, about 500 to about 750, about 750 to about 1000 or more nucleotides or residues).

An example of an amino acid modification is a conservative amino acid substitution or a deletion. In particular embodiments, a modified or variant sequence retains at least part of a function or activity of the unmodified sequence (e.g., wild-type sequence).

Another example of an amino acid modification is a targeting peptide introduced into a capsid protein of a viral particle. Peptides have been identified that target recombinant viral vectors or nanoparticles, to the central nervous system, such as vascular endothelial cells. Thus, for example, endothelial cells lining brain blood vessels can be targeted by the modified recombinant viral particles or nanoparticles.

A recombinant virus so modified may preferentially bind to one type of tissue (e.g., CNS tissue) over another type of tissue (e.g., liver tissue). In certain embodiments, a recombinant virus bearing a modified capsid protein may "target" brain vascular epithelia tissue by binding at level higher than a comparable, unmodified capsid protein. For example, a recombinant virus having a modified capsid protein may bind to brain vascular epithelia tissue at a level 50% to 100% greater than an unmodified recombinant virus.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

"Conservative variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a polypeptide indicates that a polypeptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two polypeptide sequences are identical is that one polypeptide is immunologically reactive with antibodies raised against the second polypeptide. Thus, a polypeptide is identical to a second polypeptide, for example, where the two peptides differ only by a conservative substitution.

The terms "treat" and "treatment" refer to both therapeutic treatment and prophylactic or preventative measures, wherein the object is to prevent, inhibit, reduce, or decrease an undesired physiological change or disorder, such as the development, progression or worsening of the disorder. For purposes of this invention, beneficial or desired clinical results include, but are not limited to, alleviation of symptoms, diminishment of extent of disease, stabilizing a (i.e., not worsening or progressing) symptom or adverse effect of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those predisposed (e.g., as determined by a genetic assay).

The terms "comprising," "having," "including," and "containing" are to be construed as open-ended terms (i.e., meaning "including, but not limited to") unless otherwise noted.

All methods and uses described herein can be performed in any suitable order unless otherwise indicated herein or otherwise clearly contradicted by context. The use of any and all examples, or exemplary language (e.g., "such as" or "for example") provided herein, is intended merely to better illuminate the invention and does not pose a limitation on the scope of the invention unless otherwise claimed. No language in the specification should be construed as indicating any non-claimed element as essential to the practice of the invention.

All of the features disclosed herein may be combined in any combination. Each feature disclosed in the specification may be replaced by an alternative feature serving a same, equivalent, or similar purpose. Thus, unless expressly stated otherwise, disclosed features (e.g., modified nucleic acid, vector, plasmid, a recombinant vector sequence, vector genome, or viral particle) are an example of a genus of equivalent or similar features.

As used herein, the forms "a", "and," and "the" include singular and plural referents unless the context clearly indicates otherwise. Thus, for example, reference to "a nucleic acid" includes a plurality of such nucleic acids, reference to "a vector" includes a plurality of such vectors, and reference to "a virus" or "AAV or rAAV particle" includes a plurality of such virions/AAV or rAAV particles.

The term "about" at used herein refers to a values that is within 10% (plus or minus) of a reference value.

Recitation of ranges of values herein are merely intended to serve as a shorthand method of referring individually to each separate value falling within the range, unless otherwise indicated herein, and each separate value is incorporated into the specification as if it were individually recited herein.

Accordingly, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-20, 10-50, 30-50, 50-100, 100-300, 100-1,000, 1,000-3,000, 2,000-4,000, 4,000-6,000, etc.

V. KITS

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, viral particles, splicing modifier molecules, and optionally a second active agent, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, or an electrical storage media such as RAM and ROM or hybrids of these such as magnetic/optical storage media, FLASH memory, hybrids and memory type cards.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Combined hATXN1L and miS1 Expression

Figure 4:
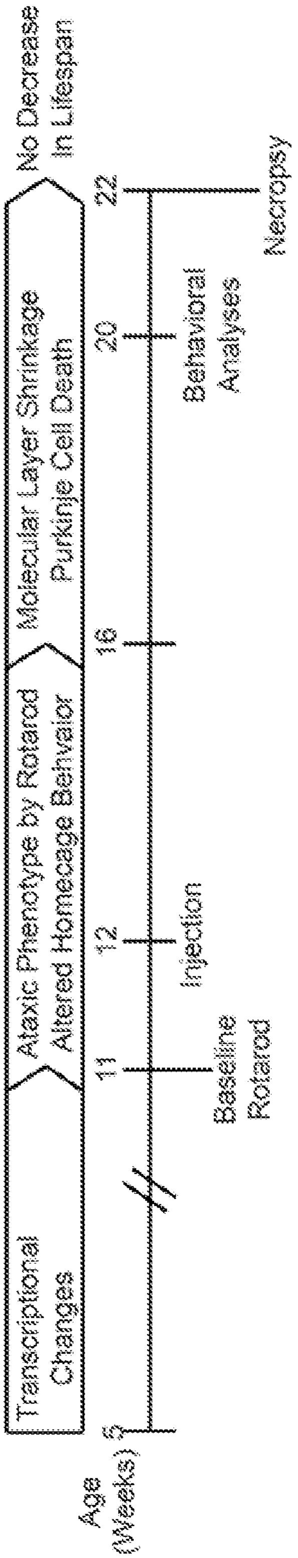
FIG. 4. Study design for B05 SCA1 mouse dosing studies.

Delivery of a single vector expressing both miS1 and ATXN1L achieves therapeutic efficacy at lower doses than either treatment alone. Delivery of lower doses provides a wider safety margin for translating these therapies to patients. To show this, bicistronic vectors expressing miS1 (5'-UCGAUCUUCAGGUCGUUGCUU-3'; SEQ ID NO: 1) and ATXN1L were generated and a dosing study was conducted in symptomatic SCA1 mice using established methods. Outcome measures include rotarod analysis and neuropathological and transcriptomics on tissues post necropsy (FIG. 4).

The dosing study tested the efficacy of AAV.miS1.ATXN1L or AAV.ATXN1L alone (constructs depicted in FIGS. 3A-B) in B05 transgenic mice (Burright et al., 1995) compared to untreated transgenic mice or wild type littermates. Animals were assayed by rotarod at 11 weeks of age prior to bilateral administration of AAV.miS1.ATXN1L or AAV.ATXN1L at escalating doses (Table 1) by stereotaxic surgery to B05 transgenic mice (FIG. 4). AAV.miS1 delivered at 8E9 vg was shown to be efficacious and well tolerated in a previous dosing study (Keiser et al., 2016). In addition, a previous study using AAV1.Ataxin-1-Like delivered at 8E9 vg prevented behavior onset (Keiser et al., 2013).

TABLE 1

AAV.miS1.Atxn1L Study Design

| Group (N = 15) | Genotype | Test Article | Dose |
|---|---|---|---|
| 1 | B05 | AAV.miS1.HAtxn1L | 8E7 vg |
| 2 | B05 | AAV.miS1.HAtxn1L | 8E8 vg |
| 3 | B05 | AAV.miS1.HAtxn1L | 8E9 vg |
| 4 | B05 | AAV.HAtxn1L | 8E7 vg |
| 4 | B05 | AAV.HAtxn1L | 8E8 vg |
| 5 | B05 | AAV.HAtxn1L | 8E9 vg |
| 6 | B05 | Saline | n/a |
| 7 | WildType | Saline | n/a |

For rotarod analysis, mice were tested by a tester blinding to the treatment groups on an accelerated rotarod apparatus. Mice were habituated to the rotarod for four minutes, then subjected to three trials per day (with at least 30 minutes of rest between trials) for four consecutive days. For each trial, acceleration was from 4 to 40 rpm over five minutes, and then speed was maintained at 40 rpm. Latency to fall (or if mice hung on for two consecutive rotations without running) was recorded for each mouse per trial. Trials were stopped at 500 seconds, and mice remaining on the rod at that time were scored as 500 seconds. Two-way analysis of variance followed by a Tukey post hoc analysis was used to assess for significant differences.

Figure 5A:
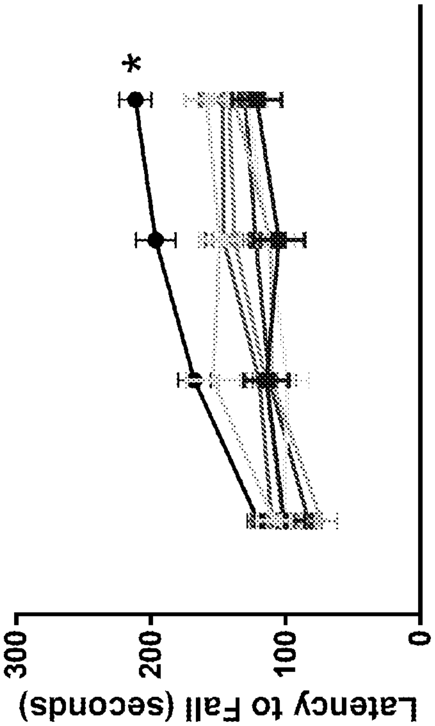
FIGS. 5A-C. Rotarod analysis.
Figure 5B:
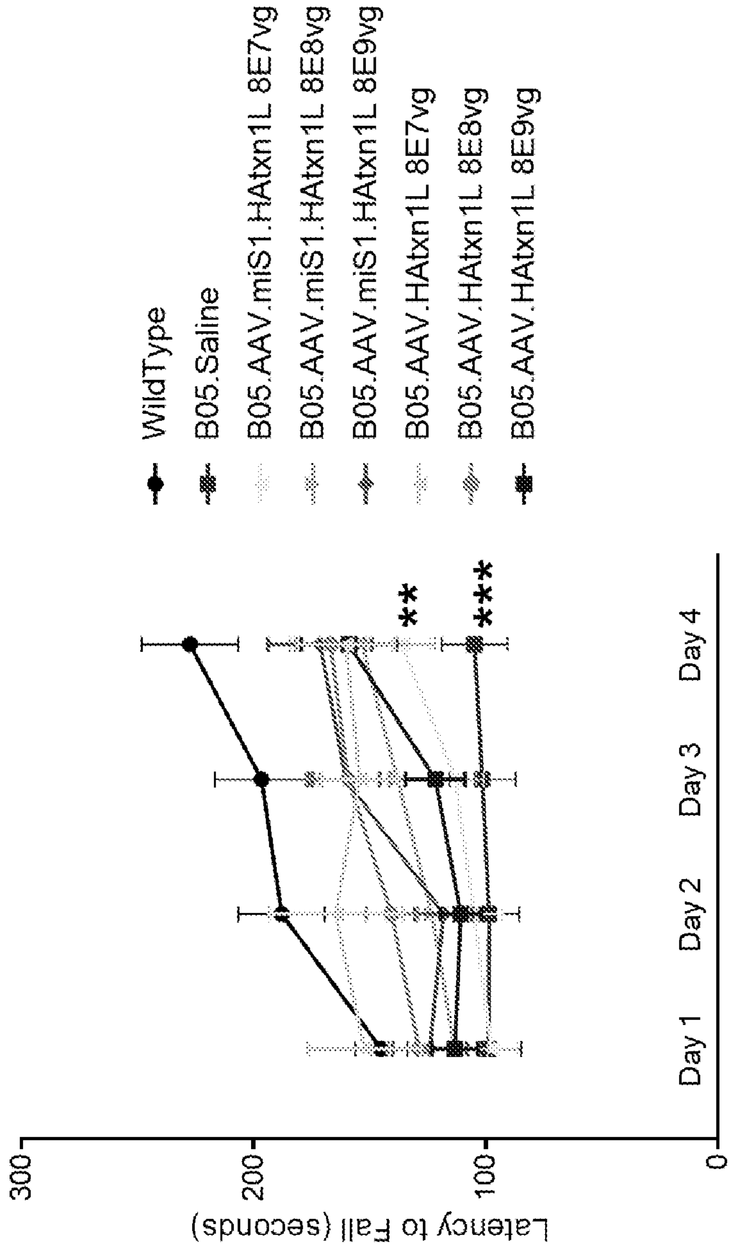
Figure 5C:
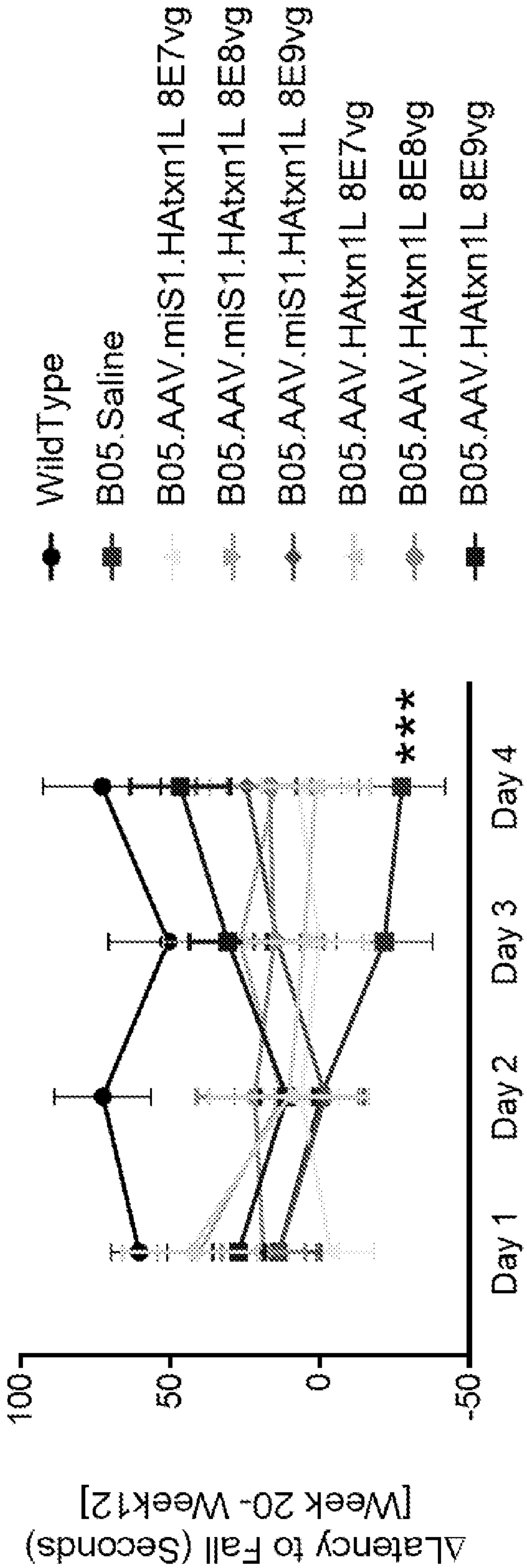

As shown in FIG. 5A, at 12 weeks of age (i.e., prior to treatment administration), B05 transgenic mice fell off the rod at a time that was statistically significantly shorter than wild-type mice. As seen in FIG. 5B, at 20 weeks of age (i.e., 8 weeks after treatment administration), control-treated transgenic mice could not remain on the rotarod apparatus after about 100 seconds. Of the B05 mice treated with AAV.miS1.HAtxn1L or AAV.HAtxn1L, only the mice treated with AAV.miS1.HAtxn1L at 8E7 vg continued to fall off the rod at a time that was statistically significantly shorter than wild-type mice. The rest of the treated mice were not statistically different than their wild-type littermates. Furthermore, as seen in FIG. 5C, when the performance of each group was analyzed as the difference in latency to fall between week 20 and week 12, only the performance of the control-treated transgenic mice was statistically lower than the wild-type mice, and only the performance of the control-treated transgenic mice worsened over time. Thus, treatment with either AAV.miS1.HAtxn1L or AAV.HAtxn1L prevents the development of further rotarod deficits in B05 mice. In addition, further analysis of the data presented in FIG. 5C shows that treatment with either AAV.miS1.HAtxn1L or AAV.HAtxn1L at the 8E9 vg dosage reversed prior rotarod deficits.

Figure 6A:
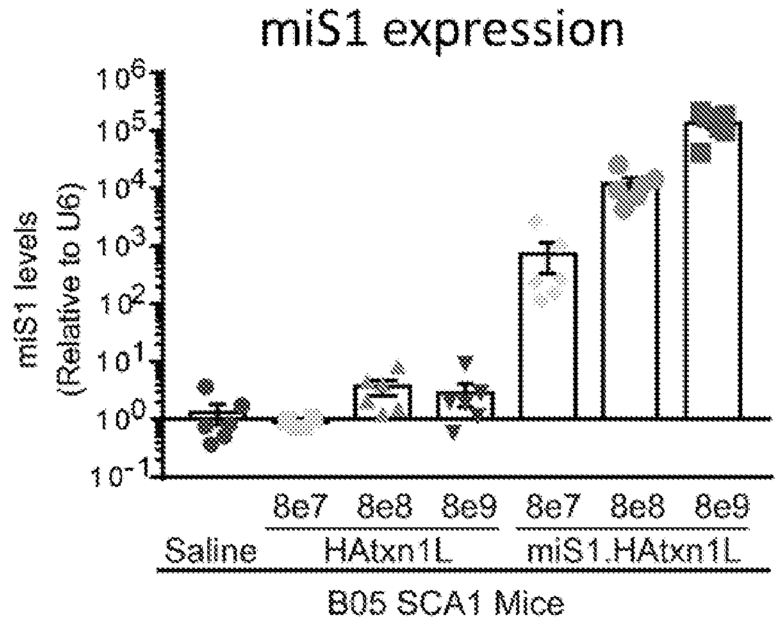
FIGS. 6A-C. qRT-PCR analyses of whole cerebellar extracts from treated B05 mice and untreated wild-type littermates.
Figure 6B:
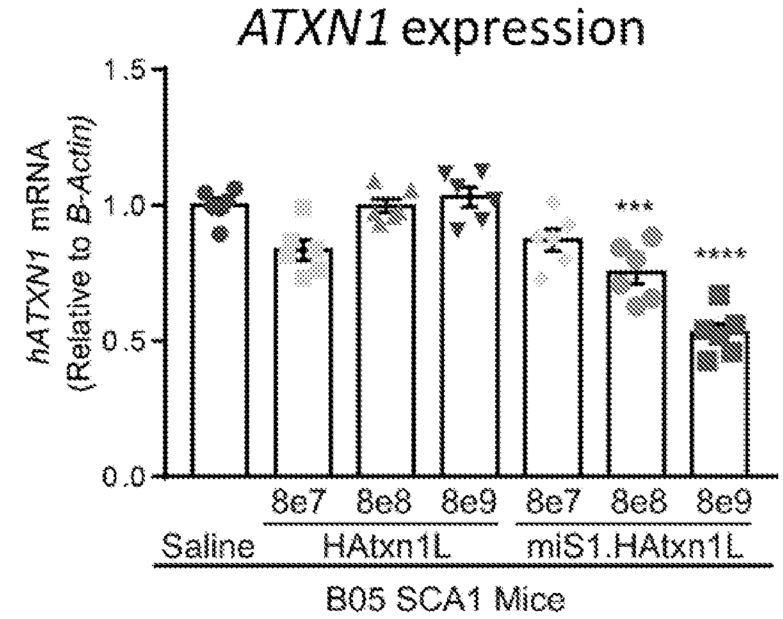
Figure 6C:
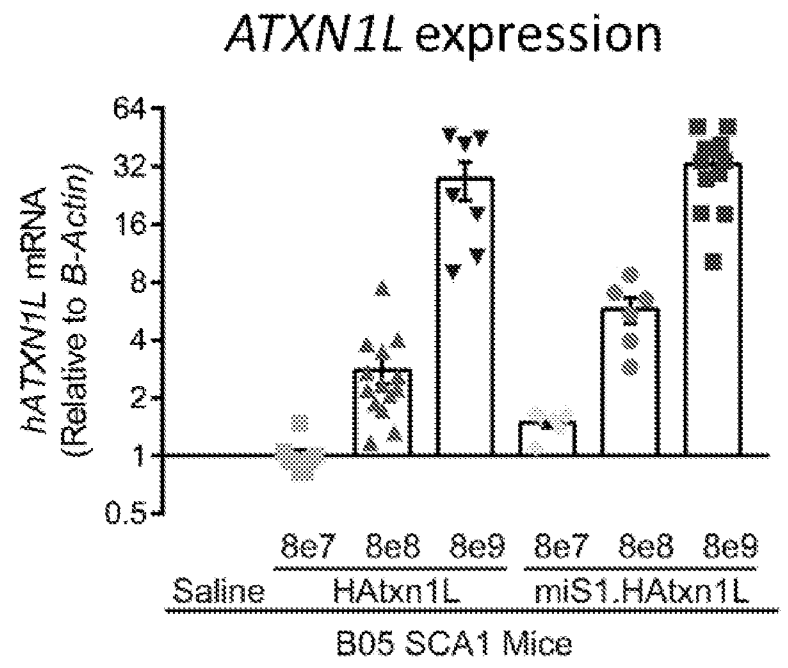

As shown in FIG. 6A, analysis of whole cerebellar lysates confirmed miS1 expression increased in a dose-dependent manner with increasing dosages of AAV.miS1.HAtxn1L. In addition, FIG. 6B shows that miS1 expression dose-dependently correlates to knockdown to Atxn1 mRNA. As shown in FIG. 6C, Atxn1L mRNA levels increased in a dose-dependent manner with increasing dosages of either AAV.miS1.HAtxn1L or AAV.HAtxn1L.

Figure 7A:
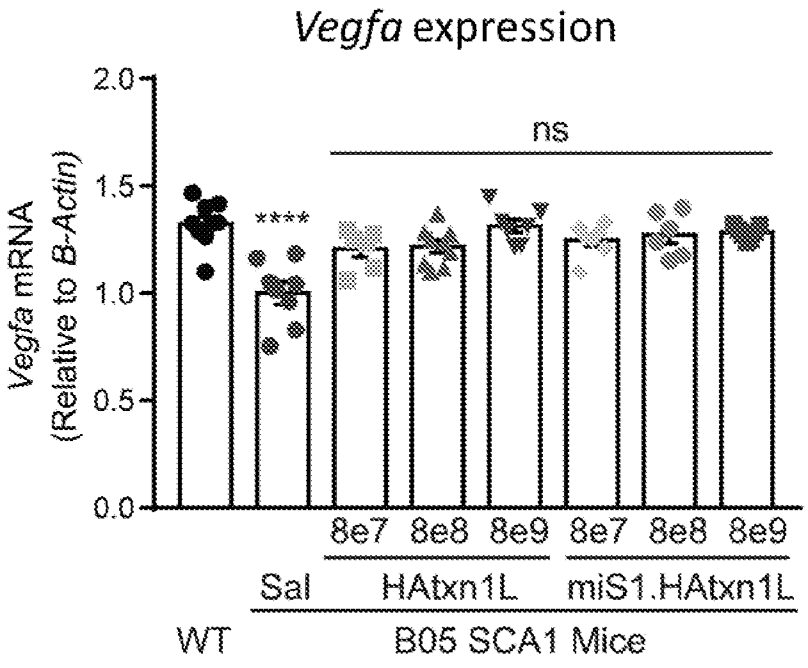
FIGS. 7A-B. qRT-PCR analysis of whole cerebellar extracts from treated B05 mice and untreated wild-type littermates to assess transcriptional dysregulation.
Figure 7B:
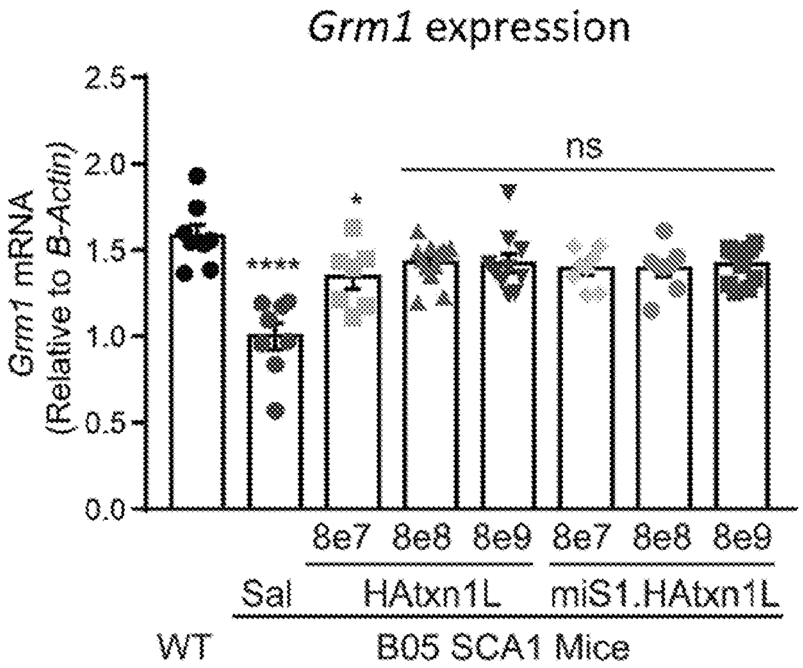

As shown in FIGS. 7A&B, evaluation of transcripts from Vegfa and the metabotropic glutamate receptor type 1 (Grm1), two transcripts downregulated in the B05 model, confirmed that mice treated with either AAV.miS1.HAtxn1L or AAV.HAtxn1L expressed Vegfa and Grm1 at levels not significantly different from wild-type mice. As such, treatment with either AAV.miS1.HAtxn1L or AAV.HAtxn1L rescues transcriptional dysregulation in symptomatic B05 mice.

Figure 8A:
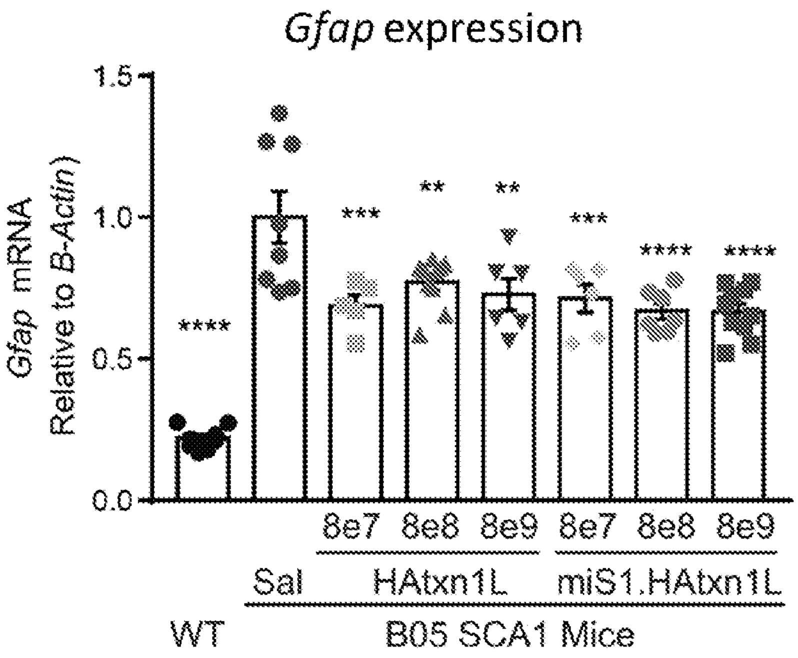
FIGS. 8A-B. qRT-PCR analysis of whole cerebellar extracts from treated B05 mice and untreated wild-type littermates to assess gliosis.
Figure 8B:
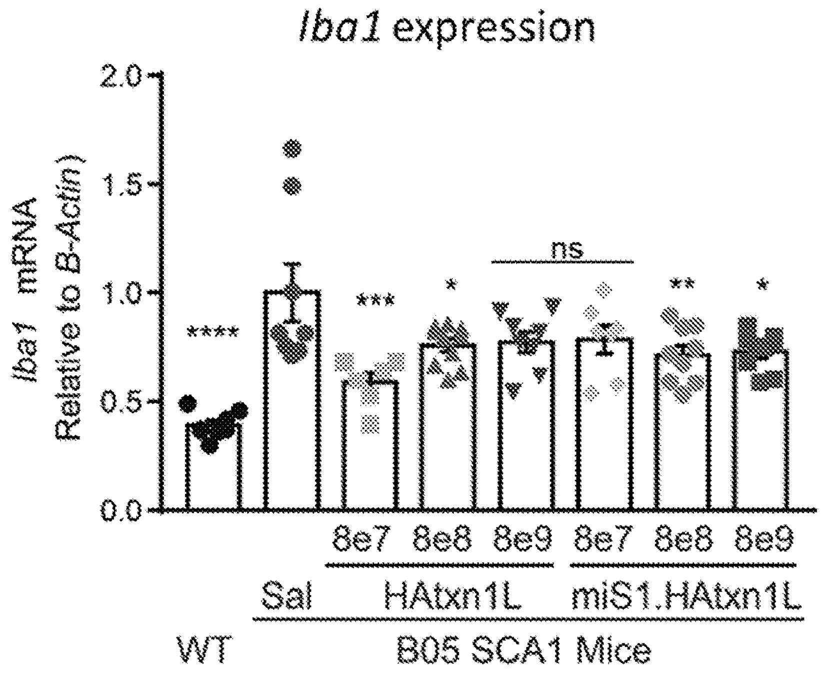

As shown in FIGS. 8A&B, treatment with either AAV.miS1.HAtxn1L or AAV.HAtxn1L rescues gliosis in B05 transgenic mice. B05 mice treated with saline showed higher levels of Gfap mRNA than those treated with either AAV.miS1.HAtxn1L or AAV.HAtxn1L (FIG. 8A). Similarly, B05 mice treated with saline showed higher levels of Iba1 mRNA than those treated with either AAV.miS1.HAtxn1L or AAV.HAtxn1L, except for mice treated with AAV.HAtxn1L at the 8E9 vg dose and mice treated with AAV.miS1.HAtxn1L at the 8E7 vg dose (FIG. 8B).

Figure 9:
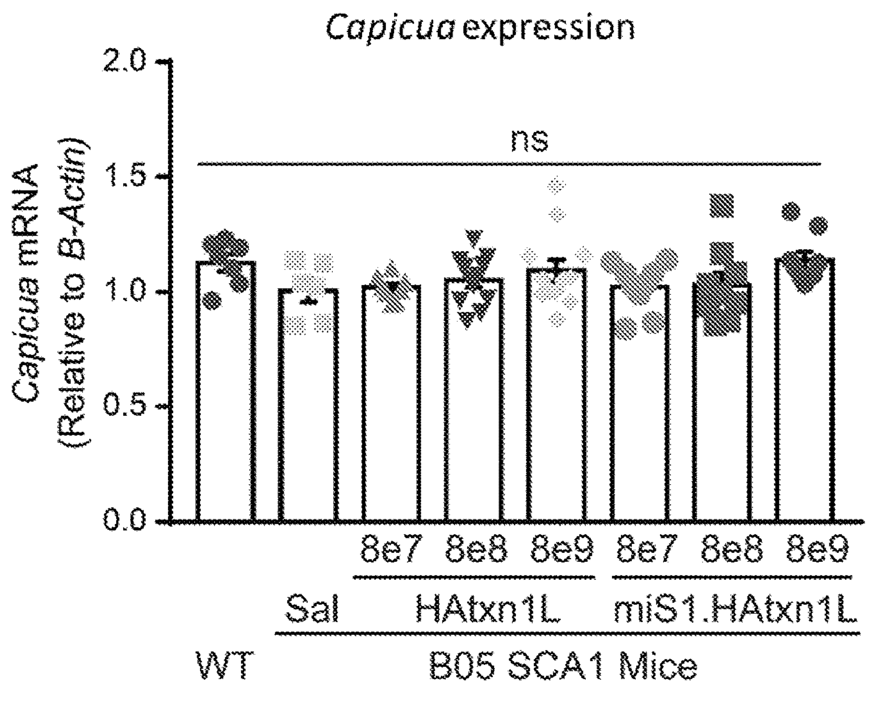
FIG. 9. qRT-PCR analysis of whole cerebellar extracts from treated B05 mice and untreated wild-type littermates to assess mouse *Capicua* levels. *p<0.05; p<0.01; *p<0.001; ****p<0.0001, relative to Saline, based on one-way ANOVA followed by Dunnett's Multiple Comparisons post hoc analysis.

As shown in FIG. 9, treatment with either AAV.miS1.HAtxn1L or AAV.HAtxn1L has no effect on normal *Capicua* mRNA levels in B05 mice.

Figure 1B:
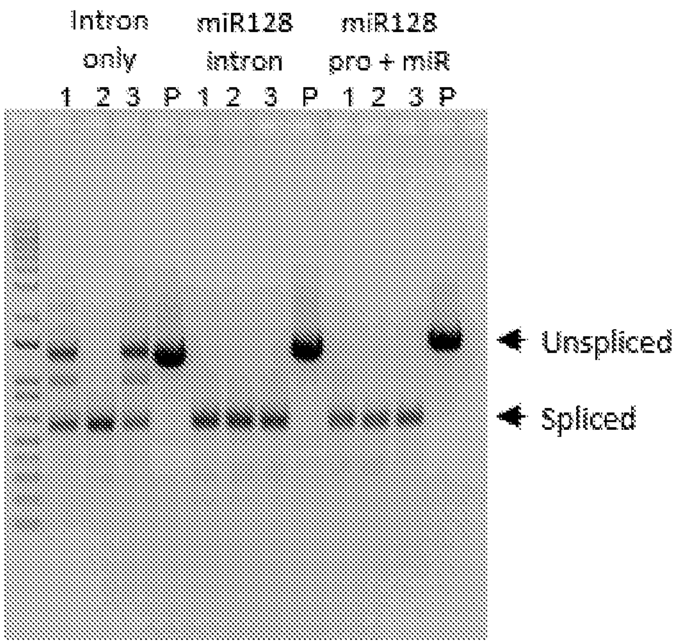
Figure 1C:
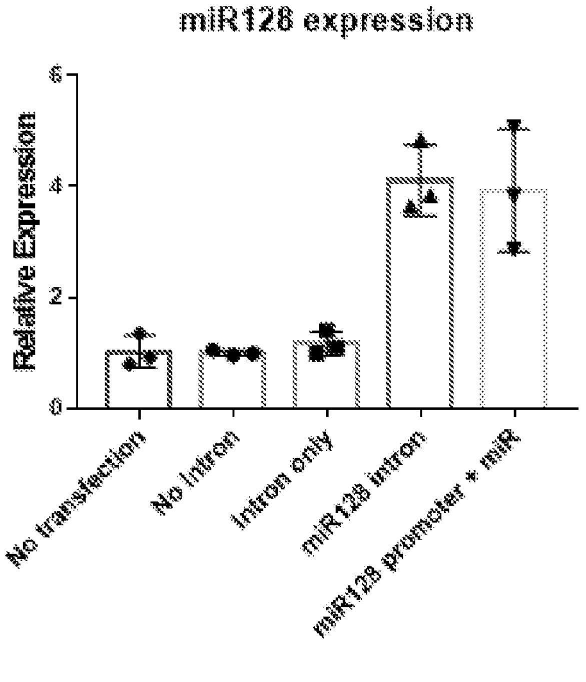
Figure 1D:
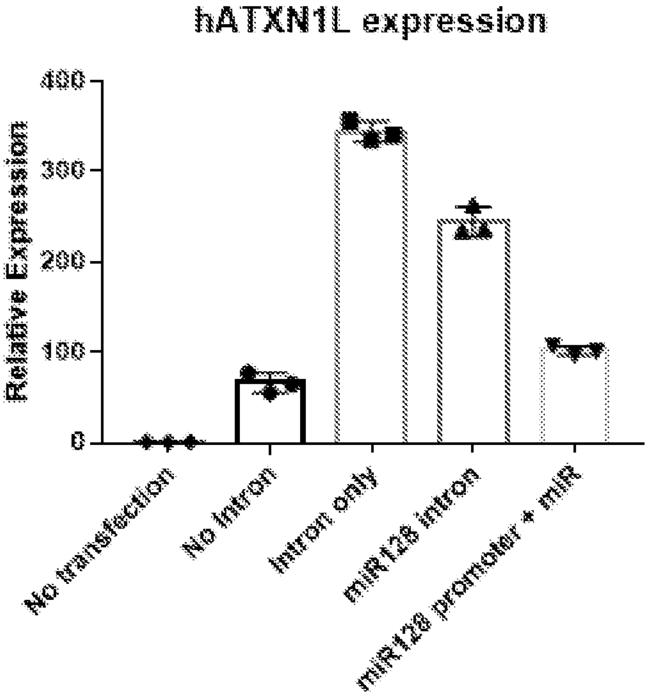

Example 2—Expression of miR128 from hATXN1L Intron 2 miR128 is a naturally occurring intronic miRNA. The proximal upstream intronic sequence (~200 bp) is sufficient to drive pol III-based expression of miR128 (Monteys et al., 2010). To test whether mature miR128 could be processed from a modified (i.e., reduced length) hATXN1L intron 2, constructs were generated as follows: (1) hATXN1L under the control of an EF1α promoter (SEQ ID NO: 2); (2) hATXN1L having an intron and under the control of an EF1α promoter (SEQ ID NO: 3); (3) hATXN1L having an intron that includes miR128 and under the control of an EF1α promoter (SEQ ID NO: 4); and (4) hATXN1L having an intron that includes miR128 along with miR128 promoter and under the control of an EF1α promoter (SEQ ID NO: 5) (see FIG. 1A). When transiently transfected into HEK293 cells, the modified intron was appropriately spliced (FIG. 1B) and miR128 was efficiently processed into a mature miRNA both with and without the miR128 promoter (FIG. 1C). Expression of hATXN1L was also assessed, and was found to be enhanced by the presence of the intron alone (FIG. 1D). However, reduced expression of hATXN1L was seen when either miR128 alone or miR128 in combination with its promoter were present in the intron (FIG. 1D), suggesting that some processing of the miRNA prior to splicing could be leading to transcript degradation by removal of the polyA tail.

Example 3—Expression of miS1 from hATXN1L Intron 2

Figure 2A:
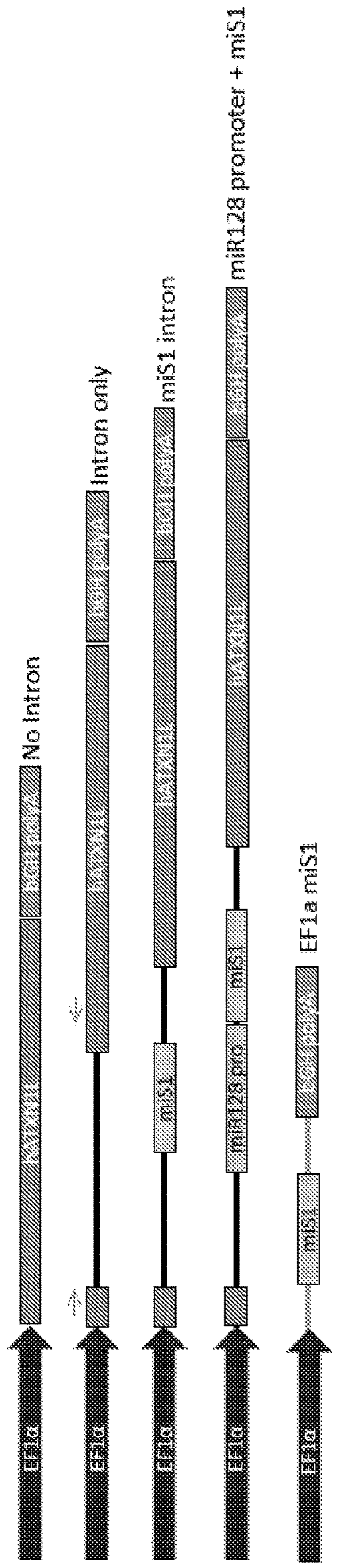
Figure 2B:
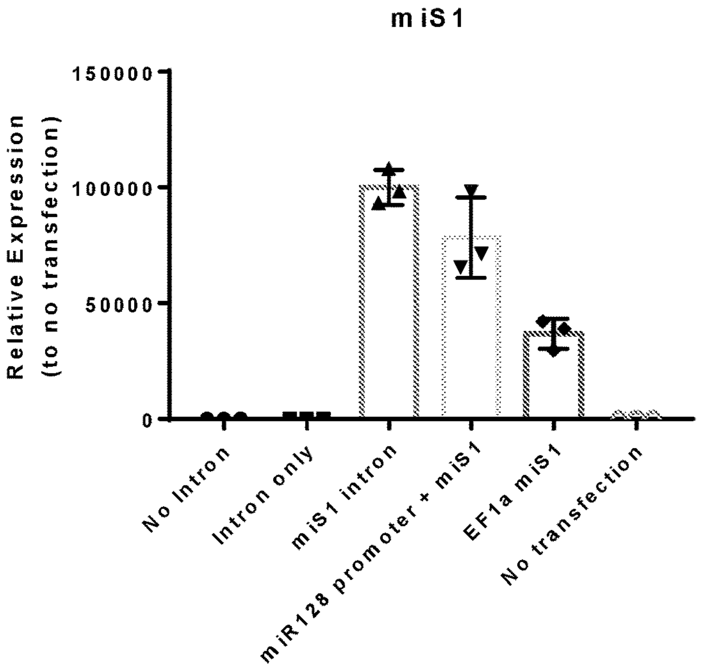
Figure 2C:
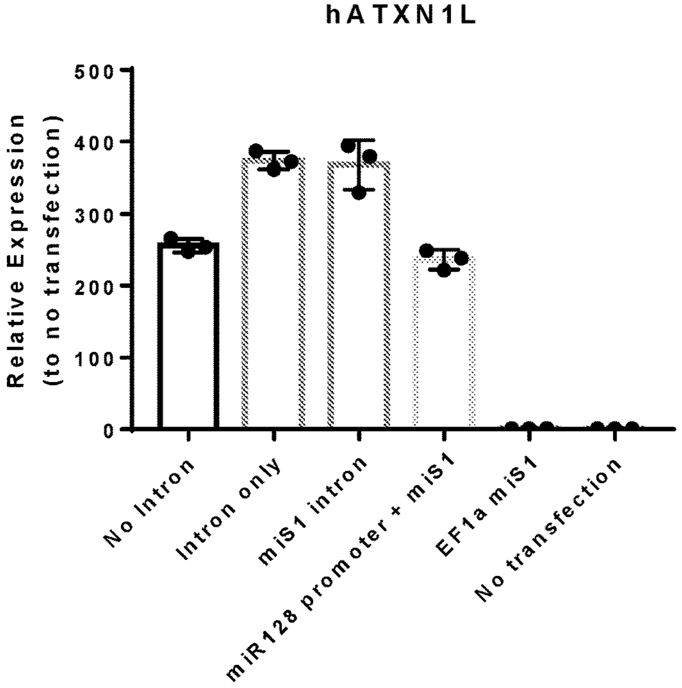

Following verification of miR128 processing from the modified hATXN1L intron 2, constructs were generated to test whether the hATXN1-targeting miRNA, miS1, could be processed from the same modified intron. To this end, constructs were generated as follows: (1) hATXN1L under the control of an EF1α promoter (SEQ ID NO: 2); (2) hATXN1L having an intron and under the control of an EF1α promoter (SEQ ID NO: 3); (3) hATXN1L having an intron that includes miS1 and under the control of an EF1α promoter (SEQ ID NO: 6); (4) hATXN1L having an intron that includes miS1 along with the miR128 promoter and under the control of an EF1α promoter (SEQ ID NO: 7); and (5) miS1 directly under the control of the EF1α promoter (SEQ ID NO: 8) (see FIG. 2A). Consistent with the miR128 results, incorporation of an intron into the hATXN1L transgene led to a significant increase in hATXN1L expression (FIG. 2C) and miS1 was effectively processed into a mature miRNA both with and without the miR128 promoter (FIG. 2B). While there was no increase in mature miS1 when the miR128 promoter was placed upstream, this may not be indicative of function in the brain since miR128 is not highly expressed in HEK293 cells. As such, it is expected that the presence of the miR128 promoter may further enhance expression of miS1 in the brain. Expression of miS1 was only modestly effective in reducing hATXN1 expression using this transient transfection assay, where only a portion of the cells are transfected (FIG. 2D). It is expected that stable expression of miS1 from AAV gene transfer into non-dividing cells will produce sufficient silencing.

Example 4—In Vivo Processing and Efficacy of miS1 from hATXN1L Intron 2

Figure 10A:
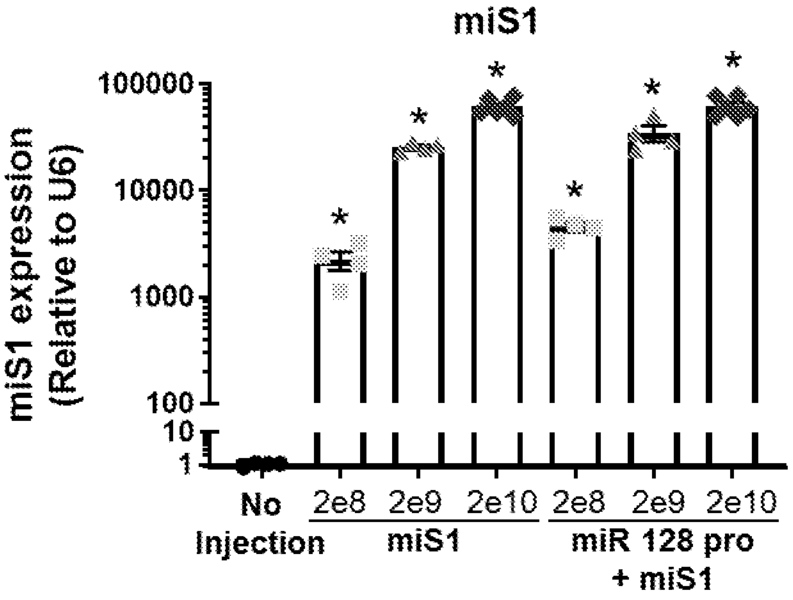
FIGS. 10A-F. qRT-PCR analysis of whole cerebellar extracts from treated B05 mice and untreated wild-type littermates to assess transgene processing and efficacy in vivo.
Figure 10B:
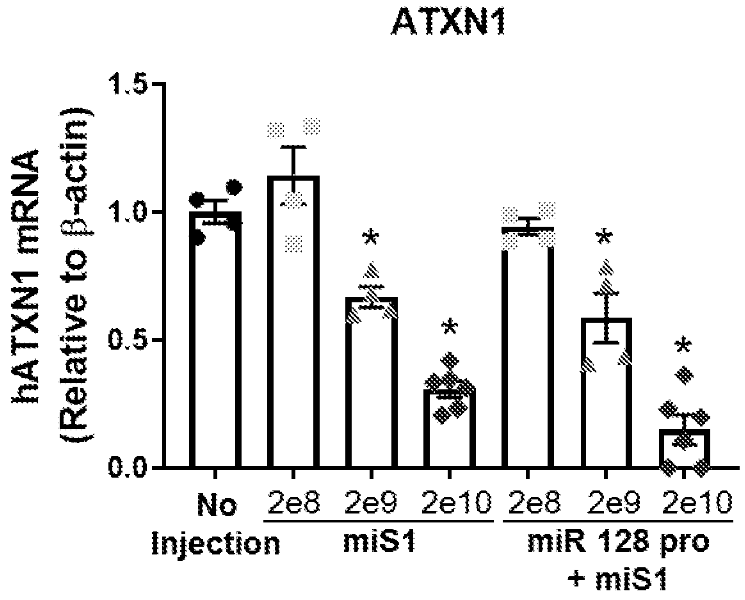
Figure 10C:
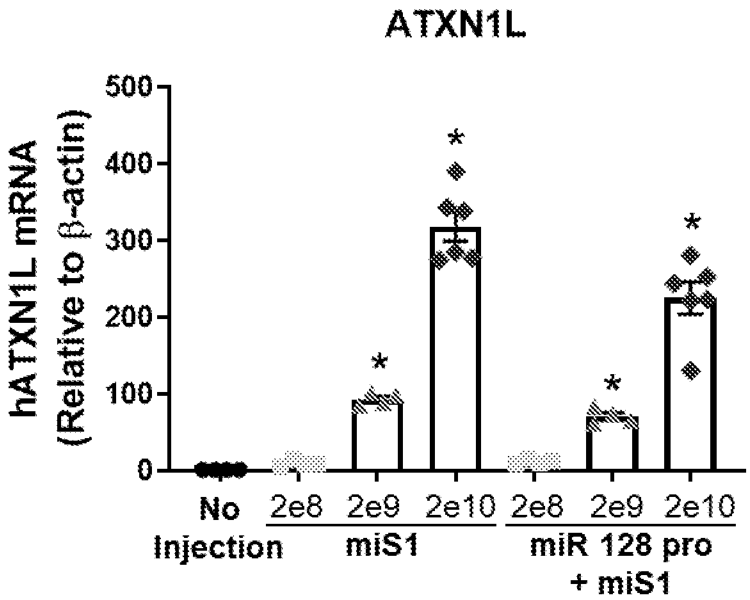
Figure 10D:
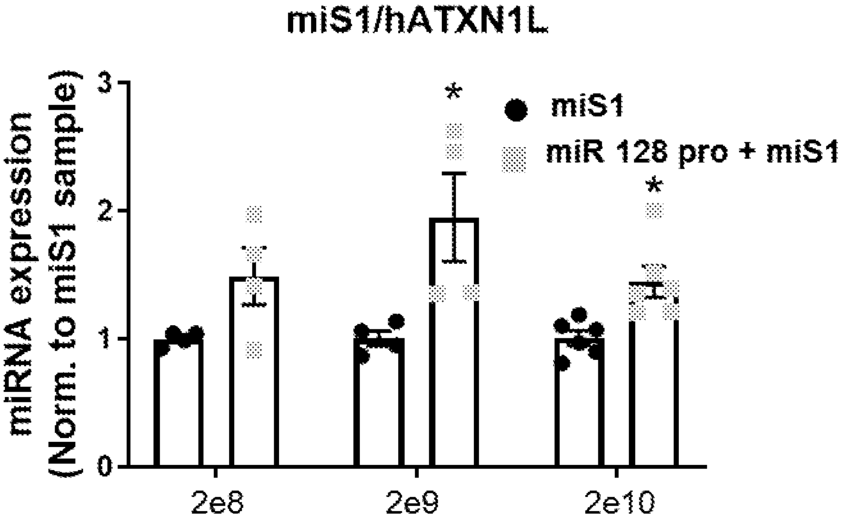
Figure 10E:
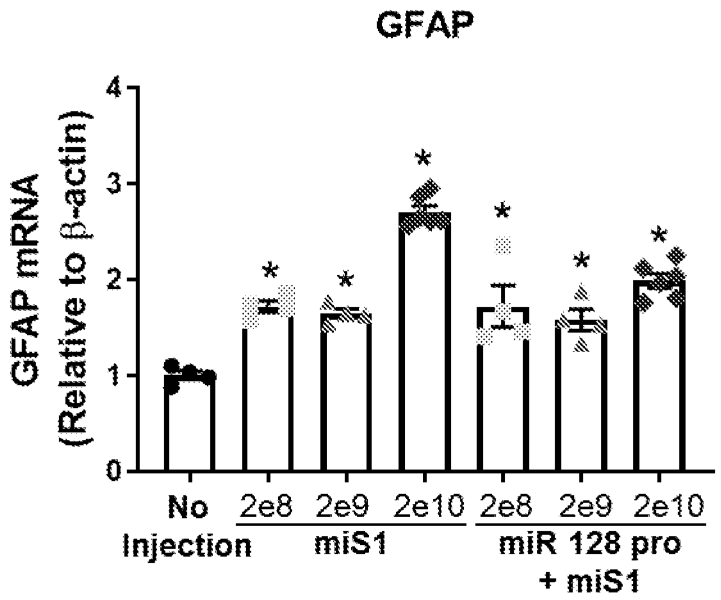
Figure 10F:
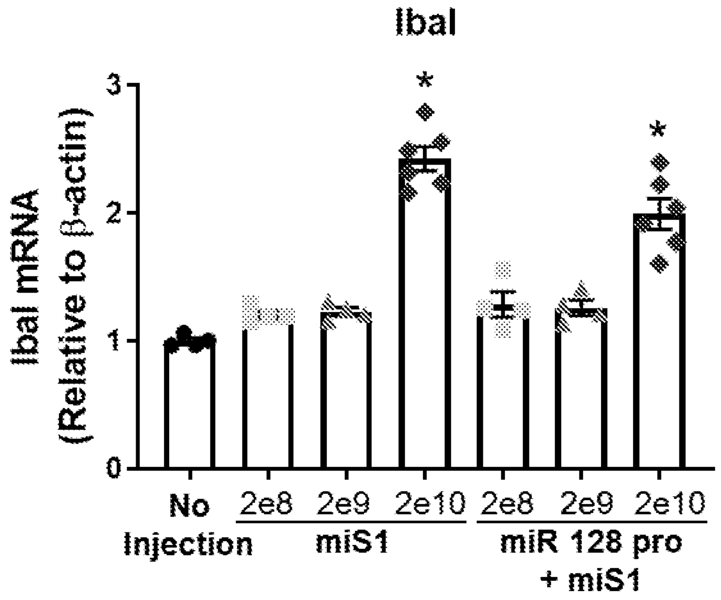

To test transgene processing and efficacy in vivo, miS1 intron or miR128 promoter+miS1 were prepared as AAV2/1 and injected into the deep cerebellar nuclei (DCN) of 6 week old B05 mice at increasing doses (2e8, 2e9, and 2e10 vg/mouse). Cerebellar hemispheres were harvested three weeks post-injection. Increasing viral dose correlated with increased miS1 expression (FIG. 10A) and a concomitant reduction in targeted hATXN1 transcripts in vivo (FIG. 10B). hATXN1L transcript levels also increased with increasing dose (FIG. 10C). Inclusion of the intronic miR128 RNA pol III promoter segment upstream the miRNA increased miS1 expression relative to hATXN1L at all doses but reached significance only at the two higher doses (FIG. 10D). Finally, B05 mice treated with either virus showed significantly increased GFAP expression, a marker of astrocytes, at all doses (FIG. 10E) while IbaI expression, a marker of microglia, was significantly increased only at the highest dose (FIG. 10F). These results demonstrate efficient combined therapy transgene processing in vivo and support virus administration at the lower doses for subsequent long-term studies.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application Publication US 2018/0169269

U.S. Patent Application Publication US 2019/0071671

Adlakha & Saini, "Brain microRNAs and insights into biological functions and therapeutic potential of brain enriched miRNA-128," Mol. Cancer, 13:33, 2014.

Banfi et al., "Identification and characterization of the gene causing type 1 spinocerebellar ataxia," Nat. Genet., 7:513-520, 1994.

Boudreau et al., "Artificial microRNAs as siRNA shuttles: improved safety as compared to shRNAs in vitro and in vivo," Mol. Ther., 17:169-175, 2009.

Bowman et al., "Duplication of Atxn1l suppresses SCA1 neuropathology by decreasing incorporation of polyglutamine-expanded ataxin-1 into native complexes," *Nat Genet,* 39:373-379, 2007.

Burright et al., "SCA1 transgenic mice: a model for neurodegeneration caused by an expanded CAG trinucleotide repeat," Cell, 82:937-948, 1995.

Cong et al., "Multiplex genome engineering using CRISPR/Cas systems," Science, 339:819-823, 2013.

Currier et al., "Spinocerebellar ataxia: study of a large kindred. I. General information and genetics," Neurology, 22:1040-1043, 1972.

Cvetanovic et al., "The role of LANP and ataxin 1 in E4F-mediated transcriptional repression," EMBO Rep., 8:671-677, 2007.

Guyenet et al., "A simple composite phenotype scoring system for evaluating mouse models of cerebellar ataxia," J. Vis. Exp., 2010(39):1787, 2010.

Jackson et al., "Spinocerebellar ataxia and HLA linkage: risk prediction by HLA typing," N. Engl. J. Med., 296:1138-1141, 1977.

Jinek et al., "RNA-programmed genome editing in human cells," Elife, 2: e00471, 2013.

Keiser et al., "RNAi or overexpression: alternative therapies for Spinocerebellar Ataxia Type 1," Neurobiol. Dis., 56:6-13, 2013.

Keiser et al., "Broad therapeutic benefit after RNAi expression vector delivery to deep cerebellar nuclei: implications for spinocerebellar ataxia type 1 therapy," Mol. Ther., 22:588-595, 2014.

Keiser et al., "RNAi prevents and reverses phenotypes induced by mutant human ataxin-1," Ann. Neurol., 80:754-765, 2016.

Kole et al. "RNA therapeutics: beyond RNA interference and antisense oligonucleotides," Nat. Rev. Drug Discov., 11:125-140, 2011.

Lai et al., "14-3-3 Binding to ataxin-1 (ATXN1) regulates its dephosphorylation at Ser-776 and transport to the nucleus," J. Biol. Chem., 286:34606-34616, 2011.

Lam et al., "ATAXIN-1 interacts with the repressor *Capicua* in its native complex to cause SCA1 neuropathology," Cell, 127:1335-1347, 2006.

Lambrechts & Carmeliet, "VEGF at the neurovascular interface: therapeutic implications for motor neuron disease," Biochim. Biophys. Acta, 1762:1109-1121, 2006.

Lim et al., "Opposing effects of polyglutamine expansion on native protein complexes contribute to SCA1," Nature, 452:713-718, 2008.

Monteys et al., "Structure and activity of putative intronic miRNA promoters," RNA, 16:495-505, 2010.

Monteys et al., "CRISPR/Cas9 Editing of the Mutant Huntingtin Allele In Vitro and In Vivo," Mol. Ther., 25:12-23, 2017.

Morrison, "The 14-3-3 proteins: integrators of diverse signaling cues that impact cell fate and cancer development," Trends Cell Biol, 19:16-23, 2009.

Orr et al., "Expansion of an unstable trinucleotide CAG repeat in spinocerebellar ataxia type 1," Nat. Genet., 4:221-226, 1993.

Orr, "Polyglutamine neurodegeneration: expanded glutamines enhance native functions," Curr. Opin. Genet. Dev., 2012. 22:251-255, 2012.
Oz et al., "Noninvasive detection of presymptomatic and progressive neurodegeneration in a mouse model of spinocerebellar ataxia type 1," J. Neurosci., 30:3831-3838, 2010.
Oz et al., "In vivo monitoring of recovery from neurodegeneration in conditional transgenic SCA1 mice," Exp Neurol, 232:290-298, 2011.
Oz et al., "Assessing recovery from neurodegeneration in spinocerebellar ataxia 1: Comparison of in vivo magnetic resonance spectroscopy with motor testing, gene expression and histology," Neurobiol. Dis., 74C: 158-166, 2014.
Ran et al., "Genome engineering using the CRISPR-Cas9 system," Nat. Protoc., 8:2281-2308, 2013.
Rodriguez-Lebron et al., "Altered Purkinje cell miRNA expression and SCA1 pathogenesis," Neurobiol. Dis., 54:456-463, 2013.
Serra et al., "Gene profiling links SCA1 pathophysiology to glutamate signaling in Purkinje cells of transgenic mice," Hum. Mol. Genet., 13:2535-2543, 2004.
Serra et al., "RORalpha-mediated Purkinje cell development determines disease severity in adult SCA1 mice," Cell, 127:697-708, 2006.
Servadio et al., "Expression analysis of the ataxin-1 protein in tissues from normal and spinocerebellar ataxia type 1 individuals," Nat. Genet., 10:94-98, 1995.
Sternberg et al., "DNA interrogation by the CRISPR RNA-guided endonuclease Cas9," Nature, 507:62-67, 2014.
Tsuda et al., "The AXH domain of Ataxin-1 mediates neurodegeneration through its interaction with Gfi-1/Senseless proteins," Cell, 122:633-644, 2005.
Xia et al., "siRNA-mediated gene silencing in vitro and in vivo," Nat. Biotechnol., 20:1006-1010, 2002.
Xia et al., "RNAi suppresses polyglutamine-induced neurodegeneration in a model of spinocerebellar ataxia," Nat. Med., 10:816-820, 2004.
Zoghbi & Orr, "Pathogenic mechanisms of a polyglutamine-mediated neurodegenerative disease, spinocerebellar ataxia type 1," J Biol Chem, 284:7425-7429, 2009.
Zu et al., "Recovery from polyglutamine-induced neurodegeneration in conditional SCA1 transgenic mice," J. Neurosci., 24:8853-8861, 2004.

What is claimed is:

1. A nucleic acid molecule comprising a first expression cassette encoding human Ataxin-1-like (hAtxn1L) and a second expression cassette encoding an inhibitory RNA targeting human ataxin-1 mRNA.

2. The nucleic acid molecule of claim 1, wherein the second expression cassette encoding an inhibitory RNA targeting human ataxin-1 mRNA is present within an intron of the first expression cassette encoding human Ataxin-1-like (hAtxn1L).

3. The nucleic acid molecule of claim 1, wherein the inhibitory RNA is a siRNA, shRNA, or miRNA.

4. The nucleic acid molecule of claim 3, wherein the inhibitory RNA is an miRNA that comprises a sequence having at least 90% identity to SEQ ID NO: 1.

5. The nucleic acid molecule of claim 1, wherein the second expression cassette encoding the inhibitory RNA comprises a promoter that is operably linked to the inhibitory RNA coding sequence.

6. The nucleic acid molecule of claim 5, wherein the promoter is a constitutive promoter, a cell-type specific promoter, or an inducible promoter.

7. The nucleic acid molecule of claim 5, wherein the promoter is a promoter for a miRNA expressed in the brain.

8. The nucleic acid molecule of claim 5, wherein the promoter is a miR128 promoter.

9. The nucleic acid molecule of claim 5, wherein the promoter has a sequence at least 90% identical to the sequence of nucleotides 1754-1931 of SEQ ID NO: 7.

10. The nucleic acid molecule of claim 1, wherein the first expression cassette encoding hAtxn1L comprises a promoter that is operably linked to the hAtxn1L coding sequence.

11. The nucleic acid molecule of claim 10, wherein the promoter is a constitutive promoter, a cell-type specific promoter, or an inducible promoter.

12. The nucleic acid molecule of claim 10, wherein the promoter has a sequence at least 90% identical to the sequence of nucleotides 194-1356 of SEQ ID NO: 7.

13. The nucleic acid molecule of claim 1, wherein the first and/or second expression cassette comprises an enhancer element.

14. The nucleic acid molecule of claim 1, wherein the first and/or second expression cassette comprises an intron, a filler polynucleotide sequence, poly A signal, or a combination thereof.

15. The nucleic acid molecule of claim 1, wherein the nucleic acid comprises a sequence at least 90% identical to the sequence of SEQ ID NO: 6 or 7.

16. An isolated cell comprising the nucleic acid molecule of claim 1.

17. A recombinant adeno-associated virus (rAAV) vector comprising an AAV capsid protein and nucleic acid molecule of claim 1.

* * * * *